US008530448B2

(12) United States Patent
Magnani et al.

(10) Patent No.: US 8,530,448 B2
(45) Date of Patent: *Sep. 10, 2013

(54) COMPOUNDS AND METHODS FOR INHIBITING SELECTIN-MEDIATED FUNCTION

(75) Inventors: John L. Magnani, Gaithersburg, MD (US); John T. Patton, Jr., Gaithersburg, MD (US); Leonard M. Williams, College Park, MD (US)

(73) Assignee: Glycomimetics, Inc., Rockville, MD (US)

( * ) Notice: Subject to any disclaimer, the term of this patent is extended or adjusted under 35 U.S.C. 154(b) by 26 days.

This patent is subject to a terminal disclaimer.

(21) Appl. No.: 12/753,452

(22) Filed: Apr. 2, 2010

(65) Prior Publication Data
US 2010/0279958 A1 Nov. 4, 2010

Related U.S. Application Data

(63) Continuation of application No. 11/411,266, filed on Apr. 26, 2006, now Pat. No. 7,741,312, which is a continuation of application No. 10/440,476, filed on May 16, 2003, now Pat. No. 7,060,685.

(60) Provisional application No. 60/381,214, filed on May 16, 2002.

(51) Int. Cl.
*A61K 31/70* (2006.01)
*C07H 15/00* (2006.01)

(52) U.S. Cl.
USPC .......... 514/54; 536/17.6; 536/123; 536/123.1

(58) Field of Classification Search
USPC .............................. 536/17.5, 17.6, 123, 123.1
See application file for complete search history.

(56) References Cited

U.S. PATENT DOCUMENTS

| | | | |
|---|---|---|---|
| 4,471,057 A | 9/1984 | Koprowski et al. | 436/518 |
| 4,851,511 A | 7/1989 | Hakomori et al. | 530/387 |
| 4,859,769 A | 8/1989 | Karlsson et al. | 536/53 |
| 4,876,199 A | 10/1989 | Hakamori | 530/387 |
| 4,925,796 A | 5/1990 | Bergh et al. | 435/97 |
| 4,946,830 A | 8/1990 | Pulverer et al. | 514/23 |
| 5,143,712 A | 9/1992 | Brandley et al. | 424/1.1 |
| 5,151,360 A | 9/1992 | Handa et al. | 435/240.2 |
| 5,211,937 A | 5/1993 | Brandley et al. | 424/1.1 |
| 5,268,364 A | 12/1993 | Kojima et al. | 514/25 |
| 5,304,640 A | 4/1994 | Lasky et al. | 536/23.5 |
| 5,352,670 A | 10/1994 | Venot et al. | 514/54 |
| 5,369,096 A | 11/1994 | Yamada et al. | 514/61 |
| 5,412,123 A | 5/1995 | Rao et al. | 552/290 |
| 5,444,050 A | 8/1995 | Kogan et al. | 514/25 |
| 5,464,778 A | 11/1995 | Cummings et al. | 436/503 |
| 5,464,815 A | 11/1995 | Chamow et al. | 514/8 |
| 5,470,843 A | 11/1995 | Stahl et al. | 514/61 |
| 5,484,891 A | 1/1996 | Lasky et al. | 530/387.3 |
| 5,486,536 A | 1/1996 | Ward et al. | 514/460 |
| 5,519,008 A | 5/1996 | Rao et al. | 514/26 |
| 5,527,785 A | 6/1996 | Bevilacqua et al. | 514/56 |
| 5,538,724 A | 7/1996 | Butcher et al. | 424/152.1 |
| 5,559,103 A | 9/1996 | Gaeta et al. | 514/54 |
| 5,576,305 A | 11/1996 | Ratcliffe | 514/25 |
| 5,580,858 A | 12/1996 | Ippolito et al. | 514/25 |
| 5,580,862 A | 12/1996 | Rosen et al. | 514/61 |
| 5,589,465 A | 12/1996 | Ishida et al. | 514/25 |
| 5,604,207 A | 2/1997 | DeFrees et al. | 514/25 |
| 5,618,785 A | 4/1997 | Heavner et al. | 514/2 |
| 5,622,937 A | 4/1997 | Kogan et al. | 514/25 |
| 5,639,734 A | 6/1997 | Esko et al. | 514/25 |
| 5,646,123 A | 7/1997 | Ippolito et al. | 514/25 |
| 5,646,248 A | 7/1997 | Sawada et al. | 530/350 |
| 5,648,344 A | 7/1997 | Brandley et al. | 514/61 |
| 5,654,282 A | 8/1997 | Tang et al. | 514/25 |
| 5,654,412 A | 8/1997 | Srivastava et al. | 536/18.5 |
| 5,658,880 A | 8/1997 | Dasgupta et al. | 514/8 |
| 5,663,151 A | 9/1997 | Martel et al. | 514/25 |
| 5,679,321 A | 10/1997 | Dasgupta et al. | 424/9.1 |
| 5,679,644 A | 10/1997 | Rao et al. | 514/26 |
| 5,686,426 A | 11/1997 | Martel et al. | 514/25 |
| 5,693,621 A | 12/1997 | Toepfer et al. | 514/25 |
| 5,695,752 A | 12/1997 | Rosen et al. | 424/94.61 |
| 5,710,023 A | 1/1998 | Collins et al. | 435/69.1 |
| 5,710,123 A | 1/1998 | Heavner et al. | 514/2 |
| 5,723,583 A | 3/1998 | Seed et al. | 530/387.3 |
| 5,728,685 A | 3/1998 | Abbas et al. | 514/53 |

(Continued)

FOREIGN PATENT DOCUMENTS

| | | |
|---|---|---|
| EP | 319253 A2 | 6/1989 |
| EP | 381 310 A1 | 8/1990 |

(Continued)

OTHER PUBLICATIONS

Abraham, W.M. et al., "Selectin Blockade Prevents Antigen-induced Late Bronchial Response and Airway Hyperresponsiveness in Allergic Sheep," *Am J. Respir Crit Care Med. 159*: 1205-1214, 1999.

Baeckström et al., "Purification and Characterization of a Membrane-bound and a Secreted Mucin-type Glycoprotein Carrying the Carcinoma-associated Sialyl-Le$^a$ Epitope on Distinct Core Proteins," *J. Biol. Chem. 266*(32):21537-21547, 1991.

Bänteli, R. et al., "Potent E-Selectin Antagonists," *Helvetica Chimica Acta 83*(11): 2893-2907, 2000.

(Continued)

*Primary Examiner* — Elli Peselev

(74) *Attorney, Agent, or Firm* — Ropes & Gray LLP

(57) ABSTRACT

Compounds and methods are provided for modulating in vitro and in vivo processes mediated by selectin binding. More specifically, selectin modulators and their use are described, wherein the selectin modulators that modulate (e.g., inhibit or enhance) a selectin-mediated function comprise a class of compounds termed BASAs (Benzyl Amino Sulfonic Acids, which include a portion or analogue thereof) linked to a carbohydrate or glycomimetic.

13 Claims, 19 Drawing Sheets

(56) References Cited

U.S. PATENT DOCUMENTS

| | | | |
|---|---|---|---|
| 5,739,300 A | 4/1998 | Toepfer et al. | 536/4.1 |
| 5,747,463 A | 5/1998 | Marinier et al. | 514/25 |
| 5,750,508 A | 5/1998 | Dasgupta et al. | 514/25 |
| 5,753,617 A | 5/1998 | Heavner et al. | 514/9 |
| 5,753,631 A | 5/1998 | Paulson et al. | 514/25 |
| 5,763,413 A | 6/1998 | Numata et al. | 514/25 |
| 5,763,582 A | 6/1998 | Rao et al. | 536/5 |
| 5,789,385 A | 8/1998 | Anderson et al. | 514/25 |
| 5,789,573 A | 8/1998 | Baker et al. | 536/24.5 |
| 5,795,958 A | 8/1998 | Rao et al. | 530/331 |
| 5,811,404 A | 9/1998 | De Frees et al. | 514/25 |
| 5,811,405 A | 9/1998 | Toepfer et al. | 514/25 |
| 5,817,742 A | 10/1998 | Toepfer et al. | 528/328 |
| 5,827,817 A | 10/1998 | Larsen et al. | 514/2 |
| 5,827,837 A | 10/1998 | Bevilacqua et al. | 514/103 |
| 5,830,871 A | 11/1998 | Wong et al. | 514/23 |
| 5,837,689 A | 11/1998 | Anderson et al. | 514/25 |
| 5,837,690 A | 11/1998 | Rao et al. | 514/26 |
| 5,840,679 A | 11/1998 | Larsen et al. | 514/8 |
| 5,854,218 A | 12/1998 | DeFrees | 514/25 |
| 5,858,983 A | 1/1999 | Seed et al. | 514/23 |
| 5,858,994 A | 1/1999 | Kretzschmar et al. | 514/62 |
| 5,880,091 A | 3/1999 | Cummings et al. | 514/8 |
| 5,916,910 A | 6/1999 | Lai | 514/423 |
| 5,919,768 A | 7/1999 | Kogan et al. | 514/25 |
| 5,919,769 A | 7/1999 | Tsukida et al. | 514/25 |
| 5,962,422 A | 10/1999 | Nagy et al. | 514/25 |
| 5,976,540 A | 11/1999 | Rittershaus et al. | 424/184.1 |
| 5,977,080 A | 11/1999 | Rosen et al. | 514/25 |
| 5,985,852 A | 11/1999 | Nagy et al. | 514/54 |
| 5,994,402 A | 11/1999 | Rotstein et al. | 514/547 |
| 6,001,819 A | 12/1999 | Simon et al. | 514/54 |
| 6,001,988 A | 12/1999 | Parma et al. | 536/24.3 |
| 6,033,665 A | 3/2000 | Yednock et al. | 424/130.1 |
| 6,037,333 A | 3/2000 | Panjwani | 514/62 |
| 6,110,897 A | 8/2000 | Unverzagt et al. | 514/25 |
| 6,111,065 A | 8/2000 | Heavner et al. | 530/300 |
| 6,120,751 A | 9/2000 | Unger | 424/9.51 |
| 6,121,233 A | 9/2000 | Magnani et al. | 514/8 |
| 6,124,267 A | 9/2000 | McEver et al. | 514/25 |
| 6,133,239 A | 10/2000 | Handa et al. | 514/25 |
| 6,133,240 A | 10/2000 | Taylor et al. | 514/25 |
| 6,136,790 A | 10/2000 | Toepfer et al. | 514/25 |
| 6,169,077 B1 | 1/2001 | Oehrlein | 514/25 |
| 6,177,547 B1 | 1/2001 | Cummings et al. | 530/388.22 |
| 6,187,754 B1 | 2/2001 | Oehrlein | 514/25 |
| 6,193,973 B1 | 2/2001 | Tuttle | 424/195.1 |
| 6,193,979 B1 | 2/2001 | Rittershaus et al. | 424/195.11 |
| 6,197,752 B1 | 3/2001 | Schmidt et al. | 514/23 |
| 6,225,071 B1 | 5/2001 | Cummings et al. | 435/7.24 |
| 6,235,309 B1 | 5/2001 | Nagy et al. | 424/450 |
| 6,280,932 B1 | 8/2001 | Parma et al. | 435/6 |
| 6,309,639 B1 | 10/2001 | Cummings et al. | 424/143.1 |
| 6,387,884 B1 | 5/2002 | Magnani et al. | 514/25 |
| 6,391,857 B1 | 5/2002 | Magnani et al. | 514/25 |
| 6,407,135 B1 | 6/2002 | Lai et al. | 514/423 |
| 6,465,434 B1 | 10/2002 | Magnani et al. | 514/23 |
| 6,492,332 B1 | 12/2002 | Demopulos et al. | 514/25 |
| 6,503,885 B1 | 1/2003 | Kiso et al. | 514/25 |
| 6,528,487 B1 | 3/2003 | Heavner et al. | 514/13 |
| 7,060,685 B2 | 6/2006 | Magnani et al. | |
| 7,741,312 B2 | 6/2010 | Magnani et al. | |
| 2001/0046970 A1 | 11/2001 | Nagy et al. | 514/53 |
| 2001/0051370 A1 | 12/2001 | Bistrup et al. | 435/193 |
| 2002/0026033 A1 | 2/2002 | Cummings et al. | 530/322 |
| 2002/0028205 A1 | 3/2002 | Holgersson et al. | 424/184.1 |
| 2002/0031508 A1 | 3/2002 | Wagner et al. | 424/94.63 |
| 2002/0040008 A1 | 4/2002 | Wagner et al. | 514/41 |
| 2002/0132220 A1 | 9/2002 | Berens et al. | 435/1.1 |
| 2002/0164336 A1 | 11/2002 | Harrison et al. | 424/146.1 |
| 2002/0164748 A1 | 11/2002 | Bistrup et al. | 435/193 |
| 2002/0168366 A1 | 11/2002 | Stewart et al. | 424/146.1 |
| 2003/0012787 A1 | 1/2003 | Ashkenazi et al. | 424/145.1 |
| 2003/0012790 A1 | 1/2003 | Ashkenazi et al. | 424/178.1 |
| 2003/0018181 A1 | 1/2003 | Larsen et al. | 536/23.4 |
| 2003/0039683 A1 | 2/2003 | Cantrell et al. | 424/450 |
| 2005/0112124 A1 | 5/2005 | Frenette et al. | |
| 2008/0112955 A1 | 5/2008 | Embury et al. | |

FOREIGN PATENT DOCUMENTS

| | | |
|---|---|---|
| EP | 408 859 A2 | 1/1991 |
| EP | 671407 A2 | 9/1995 |
| WO | WO 90/13300 | 11/1990 |
| WO | WO 91/19502 | 12/1991 |
| WO | WO 92/01718 | 2/1992 |
| WO | WO 92/07572 | 5/1992 |
| WO | WO 94/26760 | 11/1994 |
| WO | WO 94/29477 | 12/1994 |
| WO | WO 95/03059 | 2/1995 |
| WO | WO 95/29681 | 11/1995 |
| WO | WO 96/20204 | 7/1996 |
| WO | WO 96/25418 | 8/1996 |
| WO | WO 96/26950 | 9/1996 |
| WO | WO 97/01335 | 1/1997 |
| WO | WO 97/01569 | 1/1997 |
| WO | WO 97/14707 | 4/1997 |
| WO | WO 97/28173 | 8/1997 |
| WO | WO 97/28174 | 8/1997 |
| WO | WO 98/06730 | 2/1998 |
| WO | WO 98/13058 | 4/1998 |
| WO | WO 99/42130 | 8/1999 |
| WO | WO 99/43353 | 9/1999 |
| WO | WO 99/43356 | 9/1999 |
| WO | WO 01/89564 | 11/2001 |
| WO | WO 02/22820 | 3/2002 |
| WO | WO 02/062810 | 8/2002 |
| WO | WO 03/088980 | 10/2003 |
| WO | WO 03/097658 | 11/2003 |

OTHER PUBLICATIONS

Berg et al., "A Carbohydrate Domain Common to Both Sialyl Le$^a$ and Sialyl Le$^x$ Is Recognized by the Endothelial Cell Leukocyte Adhesion Molecule ELAM-1," *J. Biol. Chem.* 266(23):14869-14872, 1991.

Berg et al., "The Cutaneous Lymphocyte Antigen Is a Skin Lymphocyte Homing Receptor for the Vascular Lectin Endothelial Cell-Leukocyte Adhesion Molecule 1," *J. Exp. Med.* 174:1461-1466, 1991.

Bird and Kimber, "Oligosaccharides Containing Fucose Linked α(1-3) and α(1-4) to N-Acetylglucosamine Cause Decompaction of Mouse Morulae," *Devel. Biol.* 104:449-460, 1984.

Bjercke, J., "Rational Design and Synthesis of Oligosaccharide Mimetics: Selectin Antagonists as Cell Adhesion Inhibitors," *Abstracts of Papers, 210$^{th}$ ACS National Meeting,* American Chemical Society, Chicago, IL, Aug. 20-24, 1995, MEDI-18.

Bowen et al., "Characterization of a Human Homologue of the Murine Peripheral Lymph Node Homing Receptor," *Journal of Cell Biology* 109:421-427, 1989.

Brandley et al., "Carbohydrate Ligands of LEC Cell Adhesion Molecules," *Cell* 63:861-863, 1990.

Broquet et al., "Effect of Desipramine on a Glycoprotein Sialyltransferase Activity in C6 Cultured Glioma Cells," *J. Neurochem.* 54:388-394, 1990.

Childs et al., "High-molecular-weight glycoproteins are the major carriers of the carbohydrate differentiation antigens I, i and SSEA-1 of mouse teratocarcinoma cells," *Biochem. J.* 215:491-503, 1983.

Corral et al., "Requirements for Sialic Acid on Neutrophils in a GMP-140 (PADGEM) Mediated Adhesive Interaction with Activated Platelets," *Biochem. Biophys. Res. Commun.* 172:1349-1356, 1990.

Datta and Takayama, "Isolation and purification of trehalose 6-mono- and 6,6'-di-corynomycolates from *Cornyebacterium matruchotii.* Structural characterization of $^1$H NMR," *Carbohydrate Research* 245: 151-158, 1993.

Duijvestijn et al., "High Endothelial Differentiation in Human Lymphoid and Inflammatory Tissues Defined by Monoclonal Antibody HECA-452," *Am. J. Path.* 130:147-155, 1988.

Dupré, B. et al., "Glycomimetic Selectin Inhibitors: (α-D-Mannopyranosyloxy)methylbiphenyls," *Bioorganic & Medicinal Chemistry Letters* 6(5): 569-572, 1996.

Edgington, "How Sweet It Is: Selectin-Mediating Drugs," *Biotechnology 10*: 383-389, 1992.

Eggens et al., "A Role of Carbohydrate-Carbohydrate Interaction in the Process of Specific Cell Recognition During Embryogenesis and Organogenesis: A Preliminary Note," *Biochem. Biophys. Res. Commun. 158*(3):913-920, 1989.

Eggens et al., "Specific Interaction between Le$^x$ and Le$^x$ Determinants. A Possible Basis for Cell Recognition in Preimplantation Embryos and in Embryonal Carcinoma Cells," *J. Biol. Chem. 264*(16):9476-9484, 1989.

Ernst and Oehrlein, "Substrate and donor specificity of glycosyl transferases," *Glycoconjugate Journal 16*: 161-170, 1999.

Fenderson et al., "A Multivalent Lacto-*N*-Fucopenataose III-Lysyllysine Conjugate Decompacts Preimplantation Mouse Embryos, While the Free Oligosaccharide is Ineffective," *J. Exp. Med. 160*:1591-1596, 1984.

Fenderson et al., "Coordinate Expression of X and Y Haptens during Murine Embryogenesis," *Devel. Biol. 114*:12-21, 1986.

Fenderson et al., "The blood group I antigen defined by monoclonal antibody C6 is a marker of early mesoderm during murine embryogenesis," *Differentiation 38*:124-133, 1988.

Fukushi et al., "Novel Fucolipids Accumulating in Human Adenocarcinoma. II. Selective Isolation of Hybridoma Antibodies That Differentially Recognize Mono-, Di-, and Trifucosylated Type 2 Chain," *J. Biol. Chem. 259*(7):4681-4685, 1984.

Fukushi et al., "Novel Fucolipids Accumulating in Human Adenocarcinoma. III. A Hybridoma Antibody (FH6) Defining a Human Cancer-Associated Difucoganglioside (VI$^3$NeuAcV$^3$III$^3$Fuc$_2$nLc$_6$)," *J. Biol. Chem. 259*(16):10511-10517, 1984.

Gabius et al., "Endogenous Tumor Lectins: Overview and Perspectives," *Anticancer Res. 6*:573-578, 1986.

Gallatin et al., "A cell-surface molecule involved in organ-specific homing of lymphocyctes," *Nature 304*:30-34, 1983.

Gooi et al., "Stage-specific embryonic antigen involves α 1 → 3 fucosylated type 2 blood group chains," *Nature 292*:156-158, 1981.

Hakomori et al., "Novel Fucolipids Accumulating in Human Adenocarcinoma. I. Glycolipids With Di- or Trifucosylated Type 2 Chain," *J. Biol. Chem. 259*(7):4672-4680, 1984.

Hakomori et al., "The Hapten Structure of a Developmentally Regulated Glycolipid Antigen (SSEA-1) Isolated From Human Erythrocytes and Adenocarcinoma: A Preliminary Note," *Biochem. Biophys. Res. Comm. 100*(4):1578-1586, 1981.

Hakomori S., "Aberrant Glycosylation in Cancer Cell Membranes as Focused on Glycolipids: Overview and Perspectives," *Cancer Res. 45*:2405-2414, 1985.

Handa et al., "Selectin GMP-140 (CD62; PADGEM) Binds to Sialosyl -Le$^a$ and Sialosyl-Le$^x$, and Sulfated Glycans Modulate this Binding," *Biochemical and Biophysical Research Communication 181*(3):1223-1230, 1991.

Hansson and Zopf, "Biosynthesis of the Cancer-associated Sialyl-Le$^a$ Antigen," *Journal of Biological Chemistry 260*(16):9388-9392, 1985.

Hasegawa et al., "Synthesis of deoxy-L-fucose-containing sialyl Lewis X ganglioside analogues," *Carbohydrate Research 257*: 67-80, 1994.

Hasegawa et al., "Synthesis of sialyl Lewis X ganglioside analogues containing modified $_L$-fucose residues," *Carbohydrate Research 274*: 165-181, 1995.

Holmes et al., "Enzymatic Basis for the Accumulation of Glycolipids with X and Dimeric X Determinants in Human Lung Cancer Cells (NCI-H69)," *J. Biol. Chem. 260*(12):7619-7627, 1985.

Huse et al., "Generation of a Large Combinatorial Library of the Immunoglobulin Repertoire in Phage Lambda," *Science 246*:1275-1281, 1989.

Hynes, R., "Integrins: A Family of Cell Surface Receptors," *Cell 48*:549-554, 1987.

Issekutz, T., "Inhibition of in Vivo Lymphocyte Migration of Inflammation and Homing to Lymphoid Tissues by the TA-2 Monoclonal Antibody. A Likely Role for VLA-4 in Vivo," *Journal of Immunology 147*:4178-4184, 1991.

Itai, S. et al., "Differentiation-dependent Expression of I and Sialyl I Antigens in the Developing Lung of Human Embryos and in Lung Cancers," *Cancer Research 50*: 7603-7611, 1990.

Jeffrey et al., "Affinity Chromatography of Carbohydrate-Specific Immunoglobulins: Coupling of Oligosaccharides to Sepharose," *Biochem. Biophys. Res. Commun. 62*:608-613, 1975.

Jentsch, K.D. et al., "Inhibition of Human Immunodeficiency Virus Type I Reverse Transcriptase by Suramin-related Compounds," *The Journal of General Virology 68*(8): 2183-2192, 1987.

Kannagi et al., "New Globoseries Glycosphingolipids in Human Teratocarcinoma Reactive with the Monoclonal Antibody Directed to a Developmentally Regulated Antigen, Stage-specific Embryonic Antigen 3," *J. Biol. Chem. 258*(14):8934-8942, 1983.

Kannagi et al., "Stage-specific embryonic antigens (SSEA-3 and -4) are epitopes of a unique globo-series ganglioside isolated from human teratocarcinoma cells," *Embo J. 2*(12):2355-2361, 1983.

Karaivanova et al., "Partial Characterization of Microsomal Sialyltransferase From Chicken Liver and Hepatoma Mc-29: II. Measurement of Enzyme Activities Utilizing Microsomal Glycoproteins as Exogenous Acceptors," *Cancer Biochem. Biophys. 11*:311-315, 1990.

Kitagawa et al., "Characterization of Mucin-Type Oligosaccharides With the Sialyl-Le$^a$ Structure From Human Colorectal Adenocarcinoma Cells," *Biochem. Biophys. Res. Commun. 178*(3):1429-1436, 1991.

Kitagawa et al., "Immunoaffinity Isolation of a Sialyl-Le$^a$ Oligosaccharide from Human Milk," *J. Biochem. 104*:591-594, 1988.

Köhler and Milstein, "Continuous cultures of fused cells secreting antibody of predefined specificity," *Nature 256*:495-497, 1975.

Köhler and Milstein, "Derivation of specific antibody-producing tissue culture and tumor lines by cell fusion," *Eur. J. Immunol. 6*:511-519, 1976.

Kojima and Hakomori, "Specific Interaction between Gangliotriaosylceramide (G$_{g3}$) and Sialosyllactosylceramide (G$_{M3}$) as a Basis for Specific Cellular Recognition between Lymphoma and Melanoma Cells," *J. Biol. Chem. 264*(34):20159-20162, 1989.

Koprowski et al., "Colorectal Carcinoma Antigens Detected by Hybridoma Antibodies," *Somatic Cell Genetics 5*(6):957-972, 1979.

Korgan, T.P. et al., "Novel Synthetic Inhibitors of Selectin-Mediated Cell Adhesion: Synthesis of 1,6-Bis[3-(3-carboxymethylphenyl)-r-(2-α-$_D$-monnopyranosyloxy)phenyl]hexane (TBC1269)," *J. Med. Chem 41*:1099-1111, 1998.

Korgan, T.P. et al., "Rational Design and Synthesis of Small Molecule, Non-oligosaccharide Selectin Inhibitors: (α-D-Mannopyranosyloxy)biphenyl-Substituted Corboxylic Acids," *J. Med. Chem. 38*: 4976-4984, Dec. 22, 1995.

Kuzuoka, "Antitumor activity of murine monoclonal antibody NCC-ST-421," *Chem. Ab. 115*:27344v, 1991.

Lamblin et al., "Primary Structure Determination of Five Sialylated Oligosaccharides Derived from Bronchial Mucus Glycoproteins of Patients Suffering from Cystic Fibrosis. The Occurrence of the NeuAcα(2→3)Galβ(1→4)[Fucα(1→3)]G1cNAcβ(1→•) Structural Element Revealed by 500-Mhz H NMR Spectroscopy," *Journal of Biological Chemistry 259*(14):9051-9058, 1984.

Larsen et al., PADGEM-Dependent Adhesion of Platelets to Monocytes and Neutrophils Is Mediated by a Lineage-Specific Carbohydrate, LNF III (CD15), *Cell 63*:467-474, 1990.

Lindenberg et al., "Carbohydrate binding properties of mouse embryos," *J. Reprod. Fert. 89*:431-439, 1990.

Lipartiti et al., "Monosialoganglioside GM1 Reduces NMDA Neurotoxicity in Neonatal Rat Brain," *Experimental Neurology 113*:301-305, 1991.

Lowe et al., "A transfected human fucosyltransferase cDNA determines biosynthesis of oligosaccharide ligand(s) for endothelial-leukocyte adhesion molecule I," *Biochem. Soc. Trans. 19*(3):649-653, 1991.

Lowe et al., "ELAM-1-Dependent Cell Adhesion to Vascular Endothelium Determined by a Transfected Human Fucosyltransferase cDNA," *Cell 63*:475-484, 1990.

Macher et al., "A Novel Carbohydrate, Differentiation Antigen on Fucogangliosides of Human Myeloid Cells Recognized by Monoclonal Antibody VIM-2," *Journal of Biological Chemistry 263*(21):10186-10191, 1988.

Magnani et al., "Identification of the Gastrointestinal and Pancreatic Cancer-associated Antigen Detected by Monoclonal Antibody 19-9 in the Sera of Patients as a Mucin," *Cancer Res. 43*:5489-5492, 1983.

Magnani et al., "A Monoclonal Antibody-defined Antigen Associated with Gastrointestinal Cancer Is a Ganglioside Containing Sialylated Lacto-*N*-fucopentaose II," *Journal of Biological Chemistry 257*(23):14365-14369, 1982.

Magnani, J., "Carbohydrate Sequences Detected by Murine Monoclonal Antibodies," *Chemistry and Physics of Lipids 42*:65-74, 1986.

Mulligan and Berg, "Selection for animal cells that express the *Escherichia coli* gene coding for xanthine-gunine phosphoribosyltransferase," *Proc. Natl. Acad. Sci. USA 78*:2072-2076, 1981.

Nicolaou et al., "Total Synthesis of the Tumor-Associated $Le^x$ Family of Glycosphingolipids," *J. Amer. Chem. Soc. 112*:3693-3695, 1990.

Nudelman et al., "Novel Fucolipids of Human Adenocarcinoma: Disialosyl $Le^a$ Antigen (III$^4$FucIII$^6$NeuAcIV$^3$NeuAcLc$_4$) of Human Colonic Adenocarcinoma and the Monoclonal Antibody (FH7) Defining This Structure," *J. Biol. Chem. 261*:5487-5495, 1986.

Örhlein, R., "Carbohydrates and Derivatives as Potential Drug Candidates with Emphasis on the Selectin and Linear-B Area," *Mini Reviews in Medicinal Chemistry 1*: 349-361, 2001.

Palcic et al., "Enzymic Synthesis of Oligosaccharides Terminating in the Tumor-Associated Sialyl-Lewis-a Determinant," *Carbohydr. Res. 190*:1-11, 1989.

Palcic et al., "Regulation of N-Acetylglucosaminyltransferase V Activity. Kinetic Comparisons of Parental, Rous Sarcoma Virus-Transformed BHK, and L-Phytohemagglutinin-Resistant BHK Cells Using Synthetic Substrates and an Inhibitory Substrate Analog," *J. Biol. Chem. 265*:6759-6769, 1990.

Palcic et al., "A Bisubstrate Analog Inhibitor for $\alpha(1\rightarrow2)$-Fucosyltransferase," *J. Biol. Chem. 264*:17174-17181, 1989.

Palma-Vargas, J.M. et al., "Small-Molecule Selectin Inhibitor Protects Against Liver Inflammatory Response After Ischemia and Reperfusion," *J. Am. Coll. Surg. 185*: 365-372, 1997.

Phillips et al., "ELAM-1 Mediates Cell Adhesion by Recognition of a Carbohydrate Ligand, Sialyl-$Le^x$," *Science 250*:1130-1132, 1990.

Picker et al., "The Neutrophil Selectin LECAM-1 Presents Carbohydrate Ligands to the Vascular Selectins ELAM-1 and GMP-140," *Cell 66*:921-933, 1991.

Prokazova et al., "Sialylated lactosylceramides. Possible inducers of non-specific immunosuppression and atherosclerotic lesions," *European Journal of Biochemistry 172*:1-6, 1988.

Rauvala et al., "Studies on Cell Adhesion and Recognition. I. Extent and Specificity of Cell Adhesion Triggered by Carbohydrate-reactive Proteins (Glycosidases and Lectins) and by Fibronectin," *J. Cell Biol. 88*:127-137, 1981.

Rice and Bevilacqua, "An Inducible Endothelial Cell Surface Glycoprotein Mediates Melanoma Adhesion," *Science 246*:1303-1306, 1989.

Ruoslahti and Pierschbacher, "New Perspectives in Cell Adhesion: RGD and Integrins," *Science 238*:491-497, 1987.

Sakurai et al., "Selection of a Monoclonal Antibody Reactive with a High-Molecular-Weight Glycoprotein Circulating in the Body Fluid of Gastrointestinal Cancer Patients," *Cancer Research 48*:4053-4058, 1988.

Sastry et al., "Cloning of the immunological repertoire in *Escherichia coli* for generation of monoclonal catalytic antibodies: Construction of a heavy chain variable region-specific cDNA library," *Proc. Natl. Acad. Sci. USA 86*:5728-5732, 1989.

Scharfman, A. et al., "*Pseudomonas aeruginosa* binds to neoglycoconjugates bearing mucin carbohydrate determinants and predominantly to sialyl-Lewis x conjugates," *Glycobiology 9*(8): 757-764, 1999.

Scharfman, A. et al., "Recognition of Lewis x Derivatives Present on Mucins by Flagellar Components of *Pseudomonas aeruginosa*," *Infection and Immunity 69*(9): 5243-5248, Sep. 2001.

Shitara et al., "Application of Anti-Sialyl $Le^a$ Monoclonal antibody, KM231, for Immunotherapy of Cancer," *Anticancer Res. 11*:2003-2014, 1991.

Siuzdak et al., "Examination of the Sialyl Lewis X—Calcium Complex by Electrospray Mass Spectrometry," *Bioorganic & Medicinal Chemistry Letters 4*(24): 2863-2866, 1994.

Sprengard, U. et al., "Synthesis and Biological Activity of Novel Sialyl-Lewis$^x$ Conjugates," *Bioorganic & Medicinal Chemistry Letters 6*(5): 509-514, 1996.

Stanley and Atkinson, "The LEC11 Chinese Hamster Ovary Mutant Synthesizes *N*-Linked Carbohydrates Containing Sialylated, Fucosylated Lactosamine Units. Analysis by One- and Two-Dimensional H NMR Spectroscopy," *J. Biol. Chem. 263*(23):11374-11381, 1988.

Stephens and Cockett, "The construction of highly efficient and versatile set of mammalian expression vectors," *Nucleic Acids Research. 17*:7110, 1989.

Streeter et al., "Immunohistologic and Functional Characterization of a Vascular Addressin Involved in Lymphocyte Homing into Peripheral Lymph Nodes," *Journal of Cell Biology 107*: 1853-1862, 1988.

Stroud et al., "Extended Type 1 Chain Glycosphingolipids: Dimeric $Le^a$ (III$^4$V$^4$Fuc$_2$Lc$_6$) as Human Tumor-associated Antigen," *J. Biol. Chem. 266*(13):8439-8446, 1991.

Svenson and Lindberg, "Coupling of Acid Labile *Salmonella* Specific Oligosaccharides to Macromolecular Carriers," *J. Immunol. Meth. 25*:323-335, 1979.

Takada et al., "Adhesion of Human Cancer Cells to Vascular Endothelium Mediated by a Carbohydrate Antigen, Sialyl Lewis A$^1$," *Biochem. Biophys. Res. Commun. 179*(2):713-719, 1991.

Takeichi, M., "Cadherins: a molecular family essential for selective cell-cell adhesion and animal morphogenesis," *Trends Genet. 3*(8):213-217, 1987.

Thoma, G. et al., "A readily Available, Highly Potent E-Selectin Antagonist," *Angew. Chem. Int. Ed. 40*(19): 3644-3647, 2001.

Thoma, G. et al., "Preorganization of the Bioactive Conformation of Sialyl Lewis$^x$ Analogues Correlates with Their Affinity to E-Selectin," *Angew. Chem. Int. Ed. 40*(10): 1941-1945, 2001.

Thoma, G. et al., "Synthesis and Biological Evaluation of a Sialyl Lewis X Mimic with Significantly Improved E-selectin Inhibition," *Bioorganic & Medicinal Chemistry Letters 11*: 923-925, 2001.

Tilton, R.G., "Exdontoxin-Induced Leukocyte Accumulation in Aqueous Fluid of Rats is Decreased by a Small Molecule Selectin," *Investigative Opthalmology & Visual Science 37*(3): S918, Abstract No. 4227, Feb. 15, 1996.

Trouet et al., "A covalent linkage between daunorubicin and proteins that is stable in serum and reversible by lysosomal hydrolases, as required for a lysosomotropic drug-carrier conjugate: In vitro and in vivo studies," *Proc. Natl. Acad. Sci. USA 79*:626-629, 1982.

Tyrrell et al., "Structural requirements for the carbohydrate ligand of E-selectin," *Proc. Natl. Acad. Sci. USA 88*:10372-10376, 1991.

Waldmann, H. et al., "Synthesis of 2-Acetamindo-2-Deoxyglucosylasparagine Glyco-Tripeptide and -Pentapeptides by Selective C- and N-Terminal Elongation of the Peptide Chain," *Carbohydrate Research 196*: 75-93, 1990.

Walz et al., "Recognition by ELAM-1 of the Sialyl-$Le^x$ Determinant on Myeloid and Tumor Cells," *Science 250*:1132-1135, 1990.

Ward and Mulligan, "Blocking of adhesion molecules in vivo as anti-inflammatory therapy," *Immunology 1*: 165-171, 1994.

Whisler and Yates, "Regulation of Lymphocyte Responses by Human Gangliosides. I. Characteristics of Inhibitory Effects and the Induction of Impaired Activation," *Journal of Immunology 125*(5):2106-2111, 1980.

Yamazaki, F. et al., "Syntheisis of an appropriately protected core glycotetraoside, a key intermediate for the synthesis of 'bisected' complex-type glycans of a glycoprotein," *Carbohydrate Research 201*: 15-30, 1990.

Zhou et al., "The Selectin GMP-140 Binds to Sialylated, Fucosylated Lactosaminoglycans on Both Myeloid and Nonmyeloid Cells," *Journal of Cell Biology 115*(2):557-564, 1991.

Zopf et al., "Affinity Purification of Antibodies Using Oligosaccharide-Phenethylamine Derivatives Coupled to Sepharose," *Meth. Enzymol. 50*:171-175, 1978.

Bastin, R. et al, "Salt Selection and Optimisation Procedures for Pharmaceutical New Chemical Entities" Organic Process Research & Development (2000), vol. 4, pp. 427-435.

Belcher, J.D. et al., "Activated monocytes in sickle cell disease: potential role in the activation of vascular endothelium and vaso-occlusion," *Blood* 96(7):2451-2459, Oct. 1, 2000.

Belcher, J.D. et al., "Inflammatory response in transgenic mouse models of human sickle cell anemia," *Blood* 96(11)Pt. 1:600a, Abstract #2574, Nov. 16, 2000.

Blanc-Muesser et al., "Syntheses Stereoselective de 1-Thioglycosides," Carbohydrate Research 67:305-328, 1978.

Bock, K. et al., "Conformations in Solution of α, α-Trehalose, α-D-Glucopyranosyl α-D-Mannopyranoside, and Their 1-Thioglycosyl Analogs, and a Tentative Correlation of Their Behaviour with Respect to the Enzyme Trehalase," European Journal of Biochemistry 131:595-600, 1983.

Cao, X. et al., "Defective Lymphoid Development in Mice Lacking Expression of the Common Cytokine Receptor υ Chain," *Immunity* 2:223-238, Mar. 1995.

Ceder, O. et al., "On the Absolute Configuration of 3-Cyclohexene-1-carboxylic Acid," Acta Chemica Scandivavica 24(8):2693-2698, 1970.

Chemical Abstracts (STN), Accession No. 1997:584307, Jul. 8, 1997.

Christianson, S.W. et al., "Enhanced Human $CD4^+$T Cell Engraftment in $β_2$-Microglobulin-Deficient NOD-*scid* Mice," *The Journal of Immunology* 158:3578-3586, 1997.

Cleophax, J. et al., "A chiral synthesis of D-(+)-2,6-dideoxystreptamine and its microbial incorporation into novel antibodies," *Journal of the American Chemical Society* 98 (22): 7110-7112, Oct. 27, 1976.

Ernst B. et al., "Design and Synthesis of E-Selectin Antagonists," *Chimia* 55:268-274, 2001.

Gais, H.-J. et al., "Enantioselective and Enantioconvergent Syntheses of Building Blocks for the Total Synthesis of Cyclopentanoid Natural Products," *Angewandte Chemie, Int. Ed. Eng.* 23(2):142-143, 1984.

Harlan, J. M., "Introduction-anti-adhesion therapy in sickle cell disease," *Blood* 95:365-367, 2000.

Hebbel, P.R., "Blockade of Adhesion of Sickle Cells to Endothelium by Monoclonal Antibodies," *The New England Journal of Medicine* 342:1910-1912, Jun. 22, 2000.

Huwe, C. M. et al., "Design, Synthesis and Biological Evaluation of Aryl-substituted Sialyl Lewis X Mimetics Prepared Via Cross-metathesis of C-Fucopeptides," Biological & Medicinal Chemistry 7:773-788, 1999.

Inwald, D. P. et al., "Platelet and leucocyte activation in childhood sickle cell disease: association with nocturnal hypoxaemia," *British Journal of Haematology* 111:474-481, Nov. 2000.

Kaila, N. et al., "β-C-Mannosides as Selectin Inhibitors," Journal of Medicinal Chemistry 45(8):1563-1566, 2002.

Kaul, D.K. et al., "Hypoxia/reoxygenation causes inflammatory response in transgenic sickle mice but not in normal mice," *The Journal of Clinical Investigation* 106(3):411-420, Aug. 2000.

Kogan, T.P. et al., "Rational Design and Synthesis of Oligosaccharide Mimetics: Selectin Antagonists as Cell Adhesion Inhibitors," *Abstracts of Papers, 210th ACS National Meeting*, American Chemical Society, Chicago, IL, Aug. 20-24, 1995, MEDI-18.

Kolb, H. C. et al., "Development of Tool for the Design of Selectin Antagonists," Chem. Eur. J. 3(10):1571-1578, 1997.

Kolb, H. C. et al., "Recent progress in the glycodrug area," Pure & Applied Chemistry 69(9):1879-1884, 1997.

Matsui, N. M. et al., "The Novel Adhesion of Erythrocytes to P-Selectin in Sickle Cell.Disease," *Blood* 96(11) Pt. 1:600a, Abstract #2575, Nov. 16, 2000.

Matsui, N. M. et al., "P-selectin mediates the adhesion of sickle erythrocytes to the endothelium," *Blood* 98(6):1955-1962, Sep. 15, 2001.

Nagel, R. L., "A Knockout of a Transgenic Mouse-Animal Models of Sickle Cell Anemia," *The New England Journal of Medicine* 339:194-195, Jul. 16, 1998.

Natarajan, M.M. et al., "Adhesion of sickle red blood cells and damage to interleukin-1beta stimulated endothelial cells under flow in vitro," *Blood* 87:4845-4852, 1996.

Solovey et al., "Circulating Activated Endothelial Cells in Sickle Cell Anemia," *The New England Journal of Medicine* 337:1584-1590, Nov. 27, 1997.

Solovey et al., "Modulation of endothelial cell activation in sickle cell disease: a pilot study," *Blood* 97(7):1937-1941, Apr. 1, 2001.

Thoma, G. et al., "Synthesis and biological evaluation of a potent E-selectin antagonist," *J. Med. Chem.* 42 (23): 4909-4913, Nov. 18, 1999.

Turhan, et al., "Primary role for adherent leukocytes in sickle cell vascular occlusion: A new paradigm," *Proceedings of the National Academy of Sciences of the United States of America* 99(5):3047-3051, Mar. 5, 2002.

Lee et al., "A new method of sequencing linear oligosaccharides on gels using charged, fluorescent conjugates" Carbohydrate Research, vol. 214, 1991, pp. 155-168, XP000226749.

Payre, et al., "Chemoenzymatische Synthese eines zweifach modifizierten Pentasaccharids ale Substrat fur einen alpha-Amylase-Assay durch Fluoreszenz-loschung" Angew. Chem., vol. 107, No. 11, 1995, pp. 1361-1364.

*Results from ELISA and Cell-based flow assays*

| Compound Number | ELISA Assays | | | | Cell-based Flow Assay | | |
|---|---|---|---|---|---|---|---|
| | IC50 | rIC50 | IC50 | rIC50 | NIC % | RI% | NAC % |
| 49 | 420 | .6 | 11.3 | .509 | 13.3 | 0 | 0 |
| 54 | 525 | .63 | low | | Not tested | | |
| 52 | 264 | .3 | 22.7 | | 38 | 20.8 | 0 |
| 28 | 406 | .51 | low | | 52 (at 35 uM) | 45 (at 35 uM) | 0 |
| 50 | 181 | .26 | 18.4 | .56 | 66.4 | 71.2 | 0 |
| 51 | 200 | .29 | 8.5 | .26 | 90.9 | 92.5 | 0 |
| 13 | 695 | | | | 90.3 | 92.2 | 0 |

*FIG. 9*

COMPOUNDS AND METHODS FOR INHIBITING SELECTIN-MEDIATED FUNCTION

CROSS-REFERENCE TO RELATED APPLICATIONS

This application is a continuation of U.S. patent application Ser. No. 11/411,266 filed Apr. 26, 2006, now issued as U.S. Pat. No. 7,741,312; which application is a continuation of U.S. patent application Ser. No. 10/440,476 filed May 16, 2003, now issued as U.S. Pat. No. 7,060,685; which application claims the benefit under 35 U.S.C. §119(e) of U.S. Provisional Patent Application No. 60/381,214 filed May 16, 2002; which applications are incorporated herein by reference in their entireties.

BACKGROUND

1. Technical Field

The present invention relates generally to compounds, compositions and methods for modulating processes mediated by selectin binding, and more particularly to selectin modulators and their use, wherein the selectin modulators that modulate a selectin-mediated function comprise a class of compounds termed BASAs (Benzyl Amino Sulfonic Acids, which include a portion or analogue thereof) linked to a carbohydrate or glycomimetic.

2. Description of the Related Art

When a tissue is infected or damaged, the inflammatory process directs leukocytes and other immune system components to the site of infection or injury. Within this process, leukocytes play an important role in the engulfment and digestion of microorganisms. Thus, the recruitment of leukocytes to infected or damaged tissue is critical for mounting an effective immune defense.

Selectins are a group of structurally similar cell surface receptors that are important for mediating leukocyte binding to endothelial cells. These proteins are type 1 membrane proteins and are composed of an amino terminal lectin domain, an epidermal growth factor (EGF)-like domain, a variable number of complement receptor related repeats, a hydrophobic domain spanning region and a cytoplasmic domain. The binding interactions appear to be mediated by contact of the lectin domain of the selectins and various carbohydrate ligands.

There are three known selectins: E-selectin, P-selectin and L-selectin. E-selectin is found on the surface of activated endothelial cells, which line the interior wall of capillaries. E-selectin binds to the carbohydrate sialyl-Lewis$^x$ (SLe$^x$), which is presented as a glycoprotein or glycolipid on the surface of certain leukocytes (monocytes and neutrophils) and helps these cells adhere to capillary walls in areas where surrounding tissue is infected or damaged; and E-selectin also binds to sialyl-Lewis$^a$ (SLe$^a$), which is expressed on many tumor cells. P-selectin is expressed on inflamed endothelium and platelets, and also recognizes SLe$^x$ and SLe$^a$, but also contains a second site that interacts with sulfated tyrosine. The expression of E-selectin and P-selectin is generally increased when the tissue adjacent to a capillary is infected or damaged. L-selectin is expressed on leukocytes. Selectin-mediated intercellular adhesion is an example of a selectin-mediated function.

Modulators of selectin-mediated function include the PSGL-1 protein (and smaller peptide fragments), fucoidan, glycyrrhizin (and derivatives), anti-selectin antibodies, sulfated lactose derivatives, and heparin. All have shown to be unsuitable for drug development due to insufficient activity, toxicity, lack of specificity, poor ADME characteristics and/or availability of material.

Although selectin-mediated cell adhesion is required for fighting infection and destroying foreign material, there are situations in which such cell adhesion is undesirable or excessive, resulting in tissue damage instead of repair. For example, many pathologies (such as autoimmune and inflammatory diseases, shock and reperfusion injuries) involve abnormal adhesion of white blood cells. Such abnormal cell adhesion may also play a role in transplant and graft rejection. In addition, some circulating cancer cells appear to take advantage of the inflammatory mechanism to bind to activated endothelium. In such circumstances, modulation of selectin-mediated intercellular adhesion may be desirable.

Accordingly, there is a need in the art for identifying inhibitors of selectin-mediated function, e.g., of selectin-dependent cell adhesion, and for the development of methods employing such compounds to inhibit conditions associated with excessive selectin activity. The present invention fulfills these needs and further provides other related advantages.

BRIEF SUMMARY

Briefly stated, this invention provides compounds, compositions and methods for modulating selectin-mediated processes. In one aspect of the present invention, the compounds that modulate (e.g., inhibit or enhance) a selectin-mediated function contain a BASA (i.e., a benzyl amino sulfonic acid or portion or analogue of either) and a carbohydrate or glycomimetic. Such compounds may be combined with a pharmaceutically acceptable carrier or diluent to form a pharmaceutical composition. The compounds or compositions may be used in a method to modulate (e.g., inhibit or enhance) a selectin-mediated function, such as inhibiting a selectin-mediated intercellular adhesion.

In one aspect of the present invention, compounds are provided that contain at least two components: (1) a BASA and (2) a carbohydrate or glycomimetic (or glycoconjugate of either). Examples of a BASA are set forth below. Preferred are the BASAs shown in FIGS. 1A-1H. Examples of a carbohydrate or glycomimetic are set forth below, and include sialyl Le$^x$, sialyl Le$^a$ and glycomimetics of either. Preferred are the carbohydrates or glycomimetics shown in FIG. 1I. One compound of the present invention is a combination of a BASA and a carbohydrate or glycomimetic, to yield a compound that modulates (e.g., inhibits or enhances) a selectin-mediated function. An example of a selectin-mediated function is a selectin-mediated intercellular adhesion. Preferred compounds are compounds 60, 61, 62 and 65 as shown in FIGS. 4, 5, 6 and 7, respectively. A compound of the present invention includes physiologically acceptable salts thereof. A compound of the present invention in combination with a pharmaceutically acceptable carrier or diluent provides one composition of the present invention.

In another aspect of the present invention, methods are provided for using a compound or composition of the present invention to modulate a selectin-mediated function. Such a compound or composition can be used, for example, to inhibit or enhance a selectin-mediated function, such as selectin-mediated intercellular interactions. A compound or composition can be used in a method to contact a cell expressing a selectin in an amount effective to modulate the selectin's function. A compound or composition can be used in a method to administer to a patient, who is in need of having inhibited the development of a condition associated with an excessive selectin-mediated function (such as an excessive selectin-mediated intercellular adhesion), in an amount effective to inhibit the development of such a condition. Examples of such conditions include inflammatory diseases, autoimmune diseases, infection, cancer, shock, thrombosis, wounds, burns, reperfusion injury, platelet-mediated diseases, leukocyte-mediated lung injury, spinal cord damage, digestive tract mucous membrane disorders, osteoporosis, arthritis, asthma and allergic reactions. A compound or composition can be used in a method to administer to a patient who is the recipient of a transplanted tissue in an amount effective to inhibit rejection of the transplanted tissue. A compound or composition can be used in a method in an amount effective to target an agent to a selectin-expressing cell by contacting such a cell with the agent linked to the compound or composition. A compound or composition can be used in the manufacture of a medicament, for example for any of the uses recited above.

In another aspect of the present invention, compounds are provided (and pharmaceutical compositions thereof, uses of such compounds or compositions in the uses set forth above, and in the manufacture of medicaments) having one or more of the following structures:

(a)

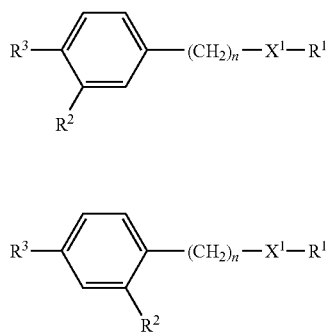

wherein n=0 or 1;

$X^1$=—$PO_2M$, —$SO_2M$, or —$CF_3$;

$R^1$=—OH or —$CO_2R^4$, wherein $R^4$=—H or —$(CH_2)_m$—$CH_3$, wherein m=0-3;

$R^2$=—H, —$PO_3M_2$, —$SO_3M_2$, —$CH_2$—$PO_3M_2$, —$CH_2$—$SO_3M_2$ or —$CF_3$

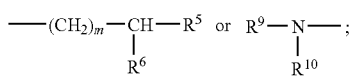

$R^5$ and $R^6$ are independently selected from —H, —$CO_2$—$R^7$ and —NH—$R^8$, wherein $R^7$ and $R^8$ are independently selected from hydrogen and moieties comprising one or more of an alkyl group, an aromatic moiety, an amino group or a carboxy group;

$R^9$ and $R^{10}$ are independently selected from —H, —$(CH_2)_m$—$CH_3$; —$CH_2$—Ar, —CO—Ar, wherein m=0-3 and Ar=an aromatic moiety; and M is selected from hydrogen, sodium, potassium and other pharmaceutically acceptable counterions; or (b)

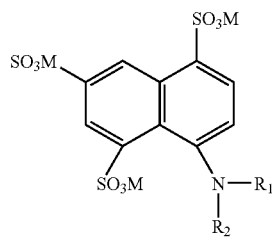

wherein $R_1$ and $R_2$ are independently selected from the group consisting of (i) hydrogen, (ii) moieties comprising one or more of an alkyl group, an aromatic moiety, an amino group or a carboxy group, and (iii) —CO—$R_3$, wherein $R_3$ comprises an aromatic moiety; and M is selected from hydrogen, sodium, potassium and other pharmaceutically acceptable counterions.

These and other aspects of the present invention will become apparent upon reference to the following detailed description and attached drawings. All references disclosed herein are hereby incorporated by reference in their entirety as if each was incorporated individually.

BRIEF DESCRIPTION OF THE SEVERAL VIEWS OF THE DRAWING(S)

FIGS. 1A-1H show structures of representative BASA components of the selectin modulators as described herein. The compounds illustrated in these figures include BASA portions and analogues. FIG. 1I shows structures of representative carbohydrate or glycomimetic components of the selectin modulators as described herein.

FIG. 9 is a table illustrating the ability of BASA analogues to inhibit P-selectin function in ELISA and cell-based assays.

DETAILED DESCRIPTION OF THE INVENTION

Figure 1A:
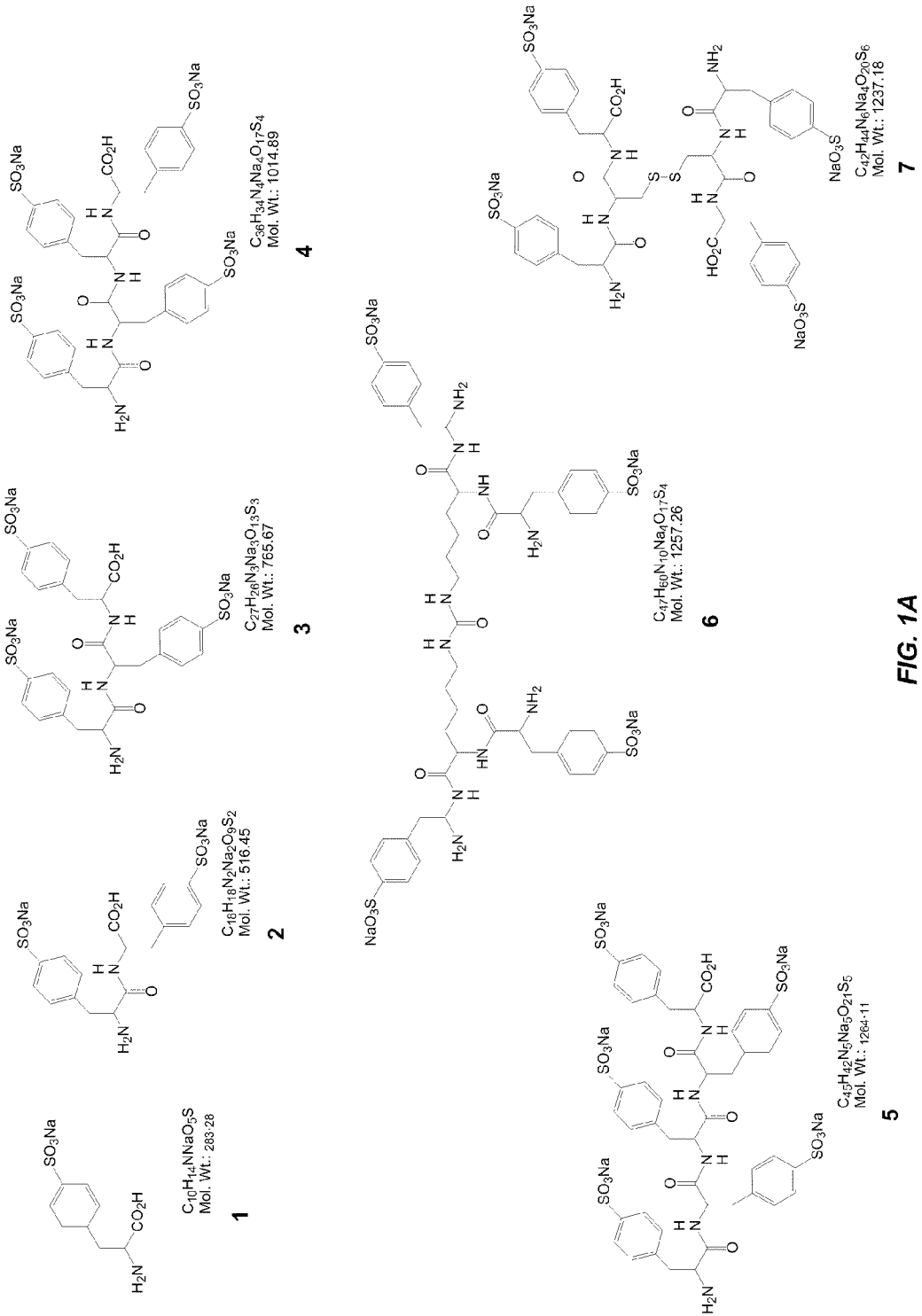
Figure 1B:
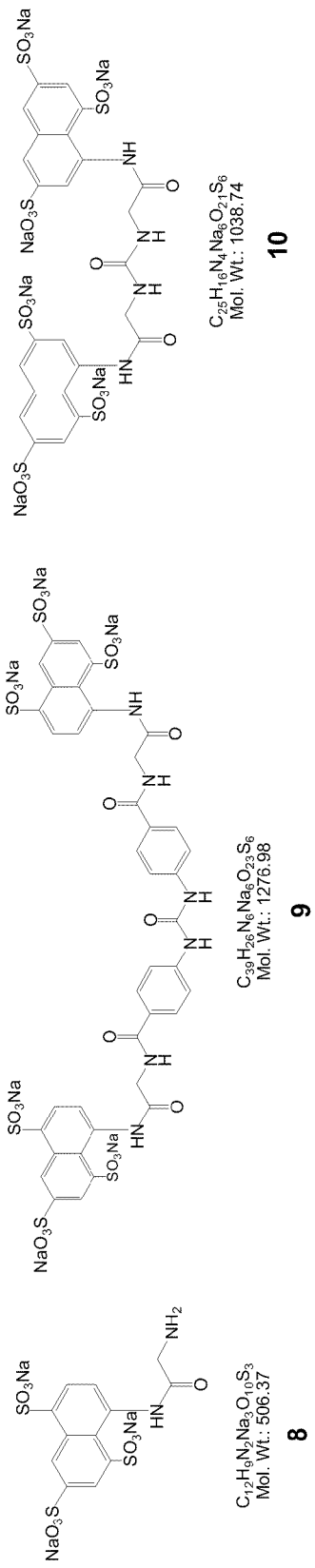
Figure 1B:
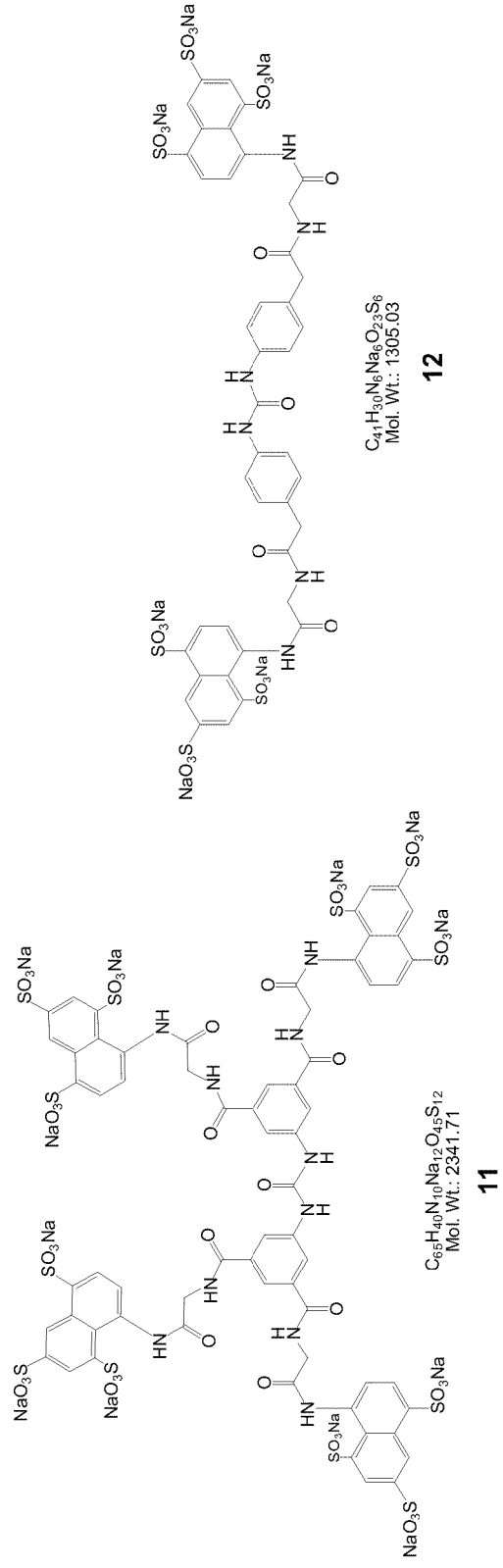
Figure 1C:
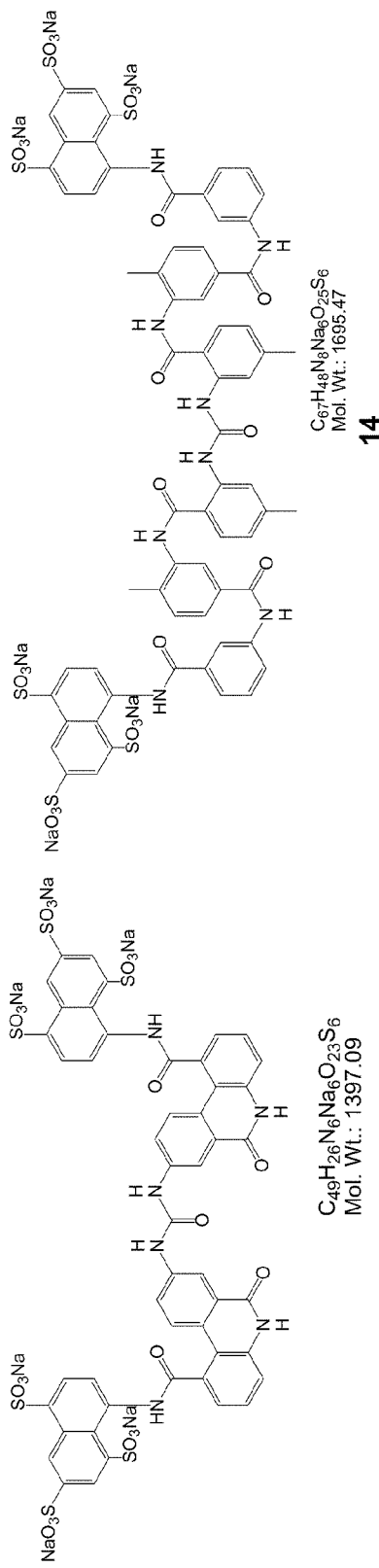
Figure 1C:
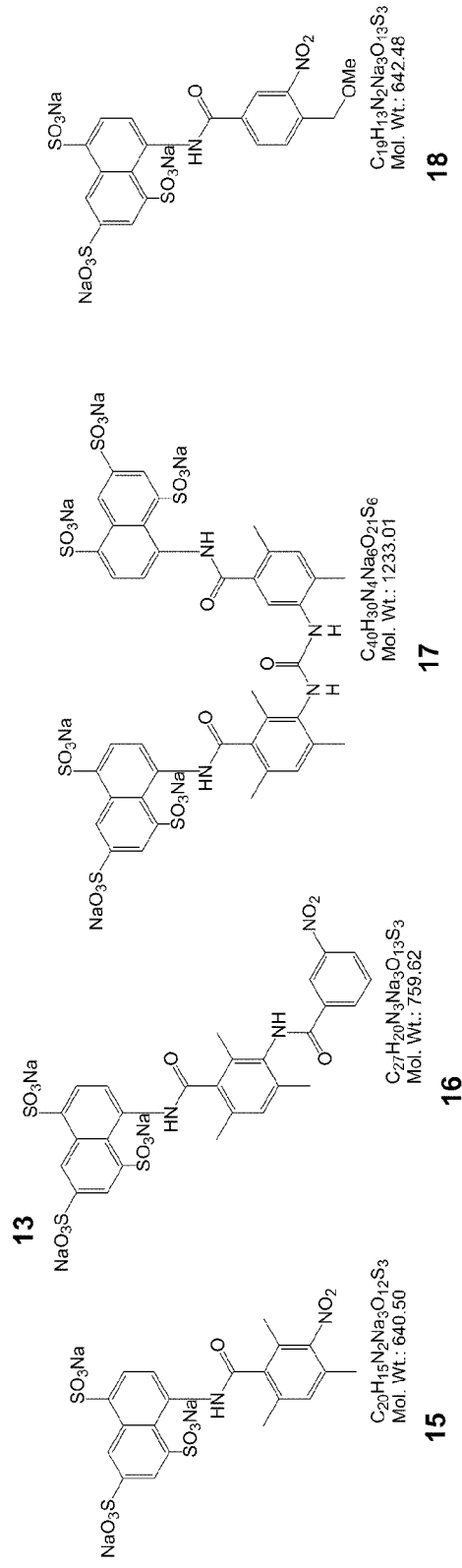
Figure 1D:
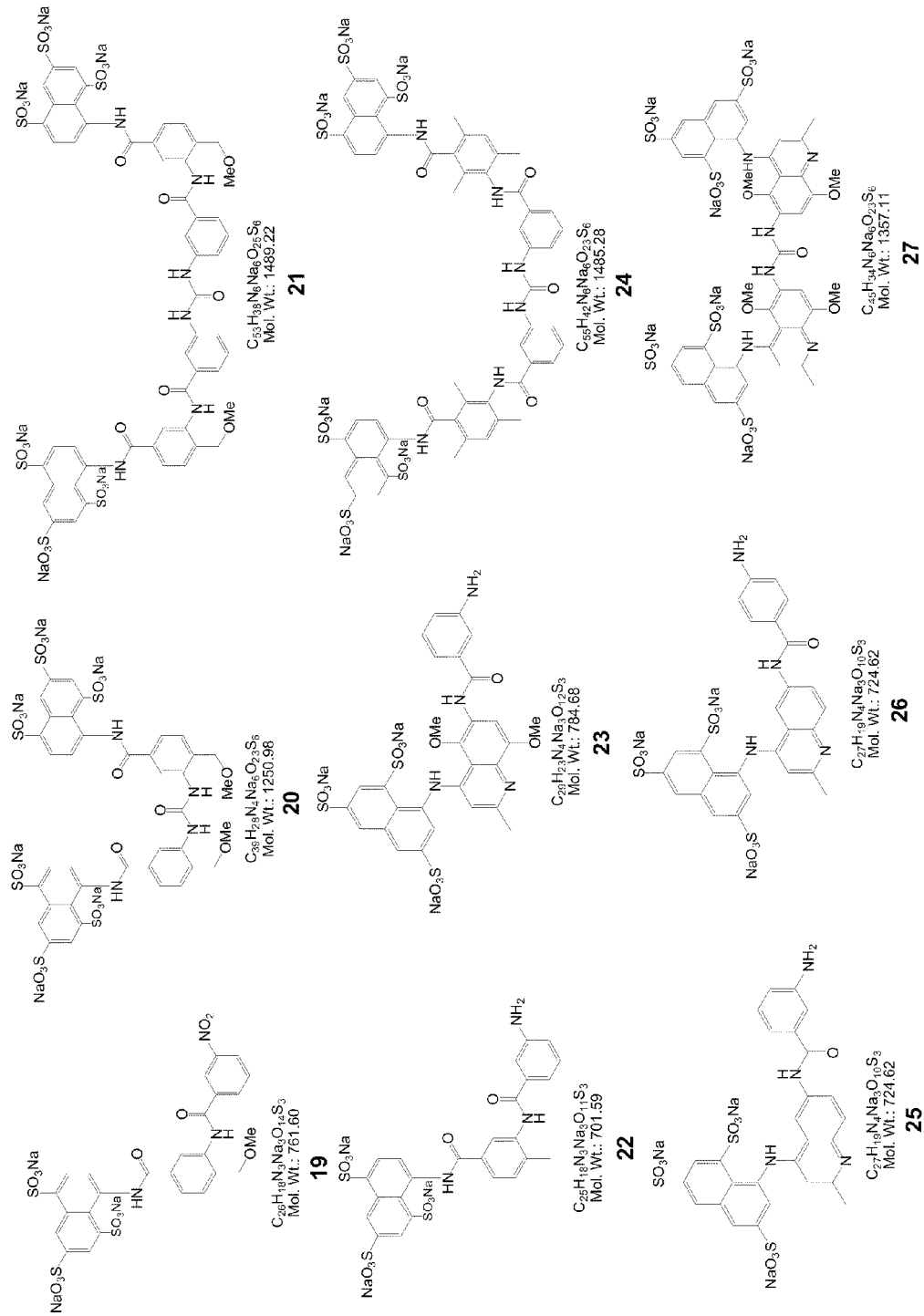
Figure 1E:
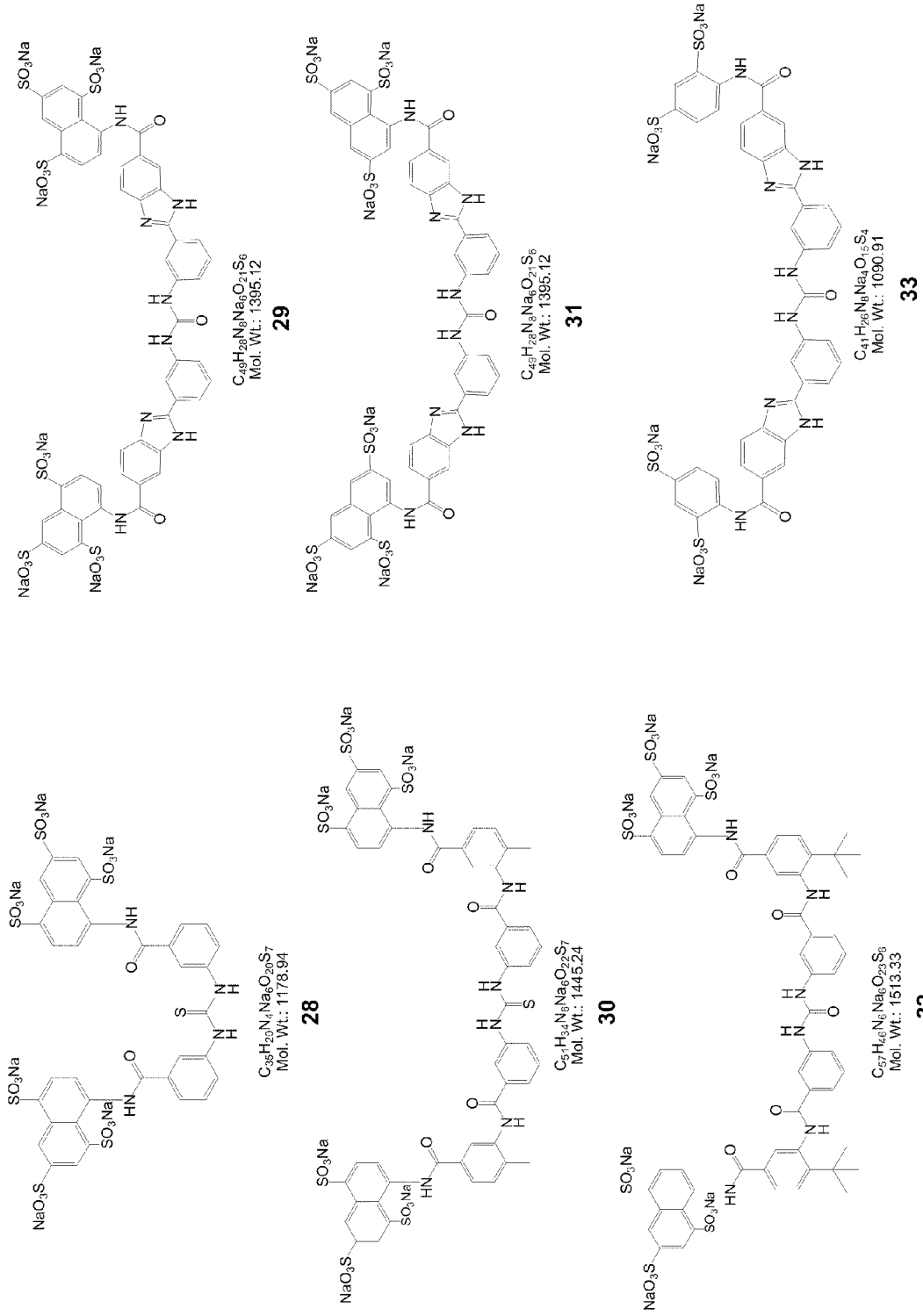
Figure 1F:
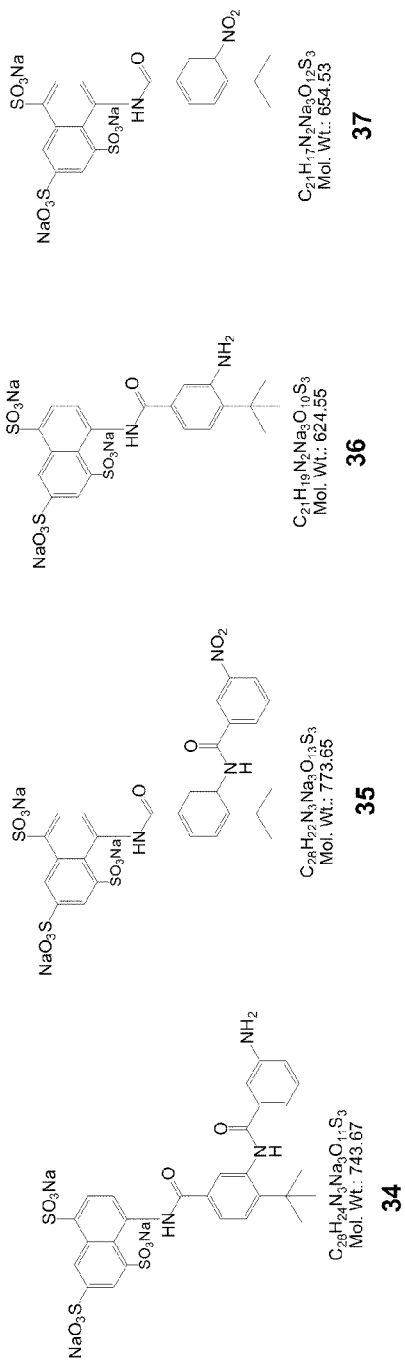
Figure 1F:
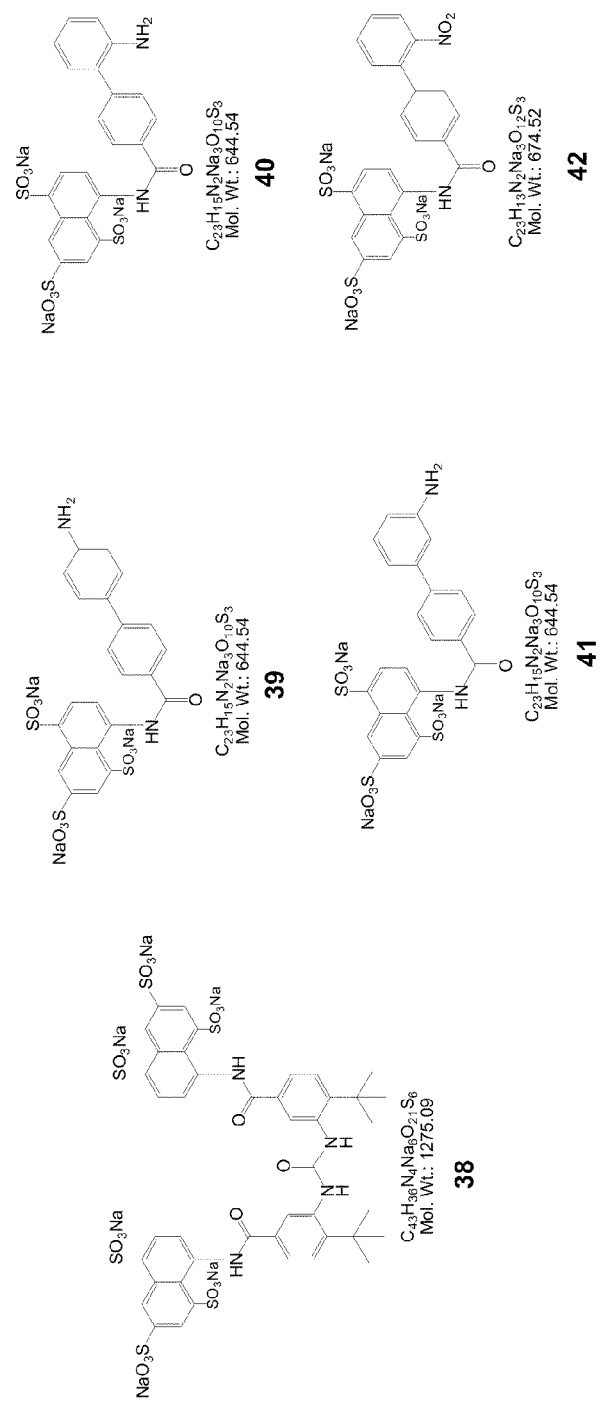
Figure 1G:
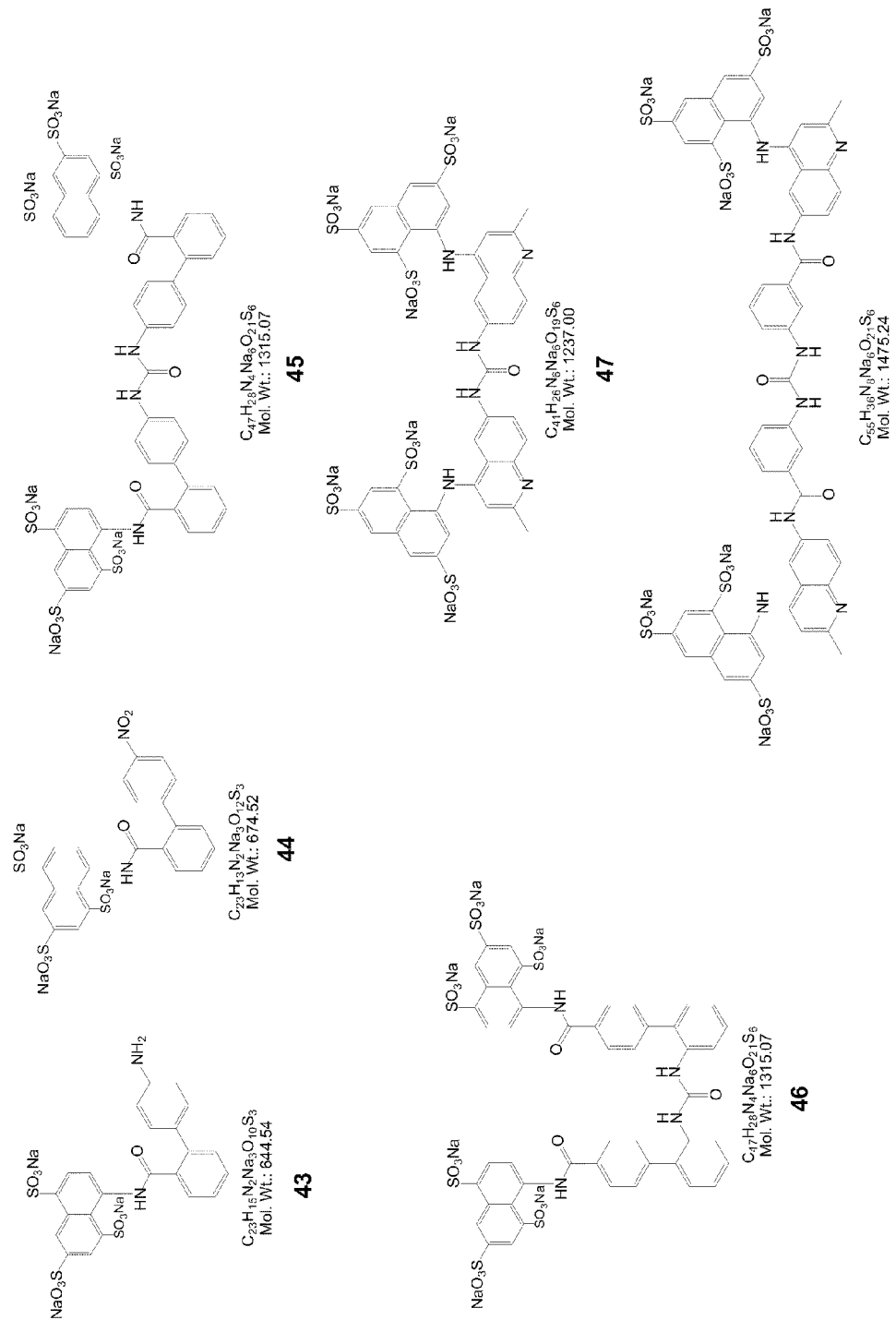
Figure 1H:
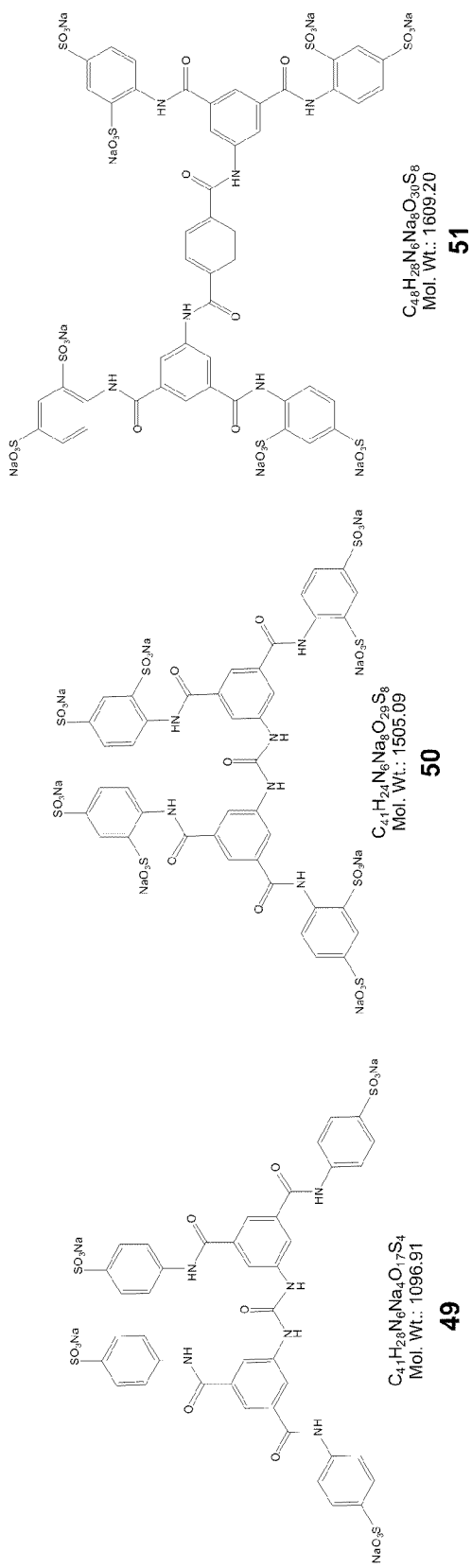
Figure 1H:
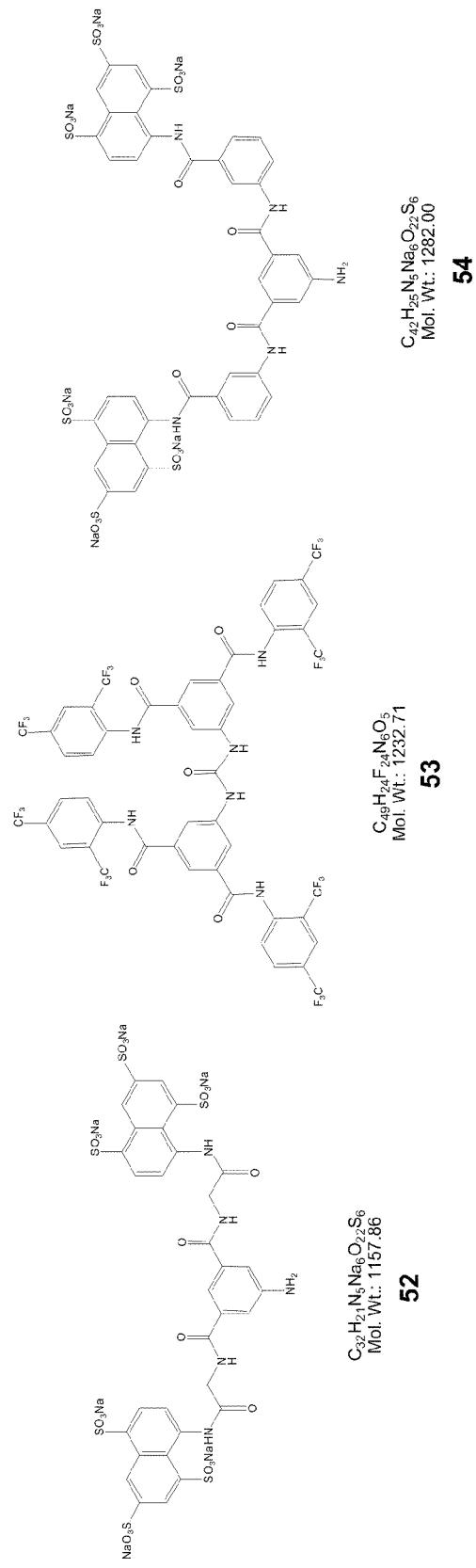

As noted above, the present invention provides, in one aspect, selectin modulators, compositions thereof and methods for modulating selectin-mediated functions. Such modulators may be used in vitro or in vivo, to modulate (e.g., inhibit or enhance) selectin-mediated functions in a variety of contexts, discussed in further detail below. Examples of selectin-mediated functions include intercellular adhesion and the formation of new capillaries during angiogenesis.

Selectin Modulators

The term "selectin modulator," as used herein, refers to a molecule(s) that modulates (e.g., inhibits or enhances) a selectin-mediated function, such as selectin-mediated intercellular interactions, and that comprises at least one of the following BASA:

(a) a BASA (or a salt thereof);
(b) a portion of a BASA that retains the ability to modulate (e.g., inhibit or enhance) a selectin-mediated function; or
(c) an analogue of a BASA, or an analogue of a portion of a BASA, that has the ability to modulate (e.g., inhibit or enhance) a selectin-mediated function;

wherein at least one of (a), (b) or (c) is linked to one or more selectin binding carbohydrate or glycomimetic (or glycoconjugates of either).

A selectin modulator may consist entirely of one or more of the above BASA elements linked to one or more carbohydrate or glycomimetic, or may comprise one or more additional molecular components. Within certain preferred embodiments, as described in more detail below, a selectin modulator comprises one of the above BASA elements linked to a carbohydrate moiety, such as sialyl-Lewis$^x$ (SLe$^x$) or sialyl-Lewis$^a$ (SLe$^a$), or linked to a glycomimetic, such as a glycomimetic of SLe$^x$ or SLe$^a$. The selectin modulators of the present invention are, surprisingly, significantly more potent than the individual components alone or additively.

Within the present invention, BASAs are low molecular weight sulfated compounds which have the ability to interact with a selectin. The interaction modulates or assists in the modulation (e.g., inhibition or enhancement) of a selectin-mediated function (e.g., an intercellular interaction). They exist as either their protonated acid form, or as a sodium salt, although sodium may be replaced with potassium or any other pharmaceutically acceptable counterion. A representative BASA has the following structure:

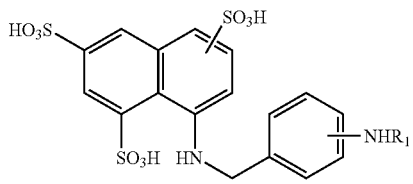

Portions of BASA that retain the ability to interact with a selectin (which interaction modulates or assists in the modulation of a selectin-mediated function as described herein) are also selectin modulators within the context of the present invention. Such portions generally comprise at least one aromatic ring present within the BASA structure. Within certain embodiments, a portion may comprise a single aromatic ring, multiple such rings or half of a symmetrical BASA molecule.

As noted above, analogues of BASA and portions thereof (both of which possess the biological characteristic set forth above) are also encompassed, e.g., by the BASA component of the selectin modulators, within the present invention. As used herein, an "analogue" is a compound that differs from BASA or a portion thereof because of one or more additions, deletions and/or substitutions of chemical moieties, such that the ability of the analogue to inhibit a selectin-mediated interaction is not diminished. For example, an analogue may contain S to P substitutions (e.g., a sulfate group replaced with a phosphate group). Other possible modifications include: (a) modifications to ring size (e.g., any ring may contain between 4 and 7 carbon atoms); (b) variations in the number of fused rings (e.g., a single ring may be replaced with a polycyclic moiety containing up to three fused rings, a polycyclic moiety may be replaced with a single unfused ring or the number of fused rings within a polycyclic moiety may be altered); (c) ring substitutions in which hydrogen atoms or other moieties covalently bonded to a carbon atom within an aromatic ring may be replaced with any of a variety of moieties, such as F, Cl, Br, I, OH, O-alkyl (C1-8), SH, $NO_2$, CN, $NH_2$, NH-alkyl (C1-8), N-(alkyl)$_2$, $SO_3M$ (where M=H$^+$, Na$^+$, K$^+$ or other pharmaceutically acceptable counterion), $CO_2M$, $PO_4M_2$, $SO_2NH_2$, alkyl (C1-8), aryl (C6-10), $CO_2$-alkyl (C1-8), —$CF_2X$ (where X can be H, F, alkyl, aryl or acyl groups) and carbohydrates; and (d) modifications to linking moieties (i.e., moieties located between rings in the BASA molecule) in which groups such as alkyl, ester, amide, anhydride and carbamate groups may be substituted for one another.

Certain BASA portions and analogues contain one of the following generic structures:

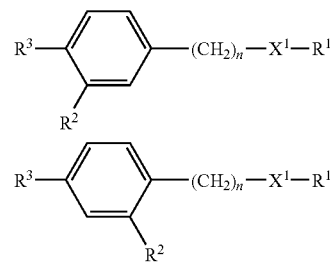

Within this structure, n may be 0 or 1, $X^1$ may be —$PO_2M$, —$SO_2M$ or —$CF_2$— (where M is a pharmaceutically acceptable counterion such as hydrogen, sodium or potassium), $R^1$ may be —OH, —F or —$CO_2R^4$ (where $R^4$ may be —H or —$(CH_2)_m$—$CH_3$ and m is a number ranging from 0 to 3, $R^2$ may be —H, —$PO_3M_2$, —$SO_3M_2$, —$CH_2$—$PO_3M_2$, —$CH_2$—$SO_3M_2$, —$CF_3$ or —$(CH_2)_m$—$C(R^6)H$—$R^5$ or $R^9$—$N(R^{10})$—, $R^3$ may be —H, —$(CH_2)_m$—$C(R^6)H$—$R^5$ or $R^9$—$N(R^{10})$— (where $R^5$ and $R^6$ may be independently selected from —H, —$CO_2$—$R^7$ and —NH—$R^8$, $R^7$ and $R^8$ may be independently selected from hydrogen and moieties comprising one or more of an alkyl group, an aromatic moiety, an amino group or a carboxy group, and $R^9$ and $R^{10}$ may be independently selected from —H, —$(CH_2)_m$—$CH_3$; —$CH_2$—Ar, —CO—Ar, where m is a number ranging from 0 to 3 and Ar is an aromatic moiety (i.e., any moiety that comprises at least one substituted or unsubstituted aromatic ring, wherein the ring is directly bonded to the —$CH_2$— or —CO— group indicated above)).

Other portions and analogues of BASA comprise the generic structure:

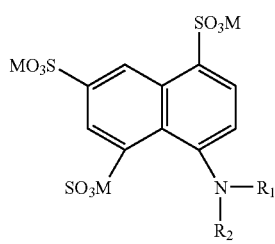

Within this structure, $R_1$ and $R_2$ may be independently selected from (i) hydrogen, (ii) moieties comprising one or more of an alkyl group, an aromatic moiety, an amino group or a carboxy group, and (iii) —CO—$R_3$ (where $R_3$ comprises an alkyl or aromatic moiety as described above) and M is a pharmaceutically acceptable counterion.

The individual compounds, or groups of compounds, derived from the various combinations of the structures and substituents described herein, are disclosed by the present application to the same extent as if each compound or group of compounds was set forth individually. Thus, selection of particular structures and/or particular substituents is within the scope of the present invention.

Representative BASA portions and analogues are included in the compounds shown in FIGS. 1A-1H. It will be apparent to those of ordinary skill in the art that modifications may be made to the compounds shown within these figures, without adversely affecting the ability to function as selectin modulators. Such modifications include deletions, additions and substitutions as described above.

Figure 2:
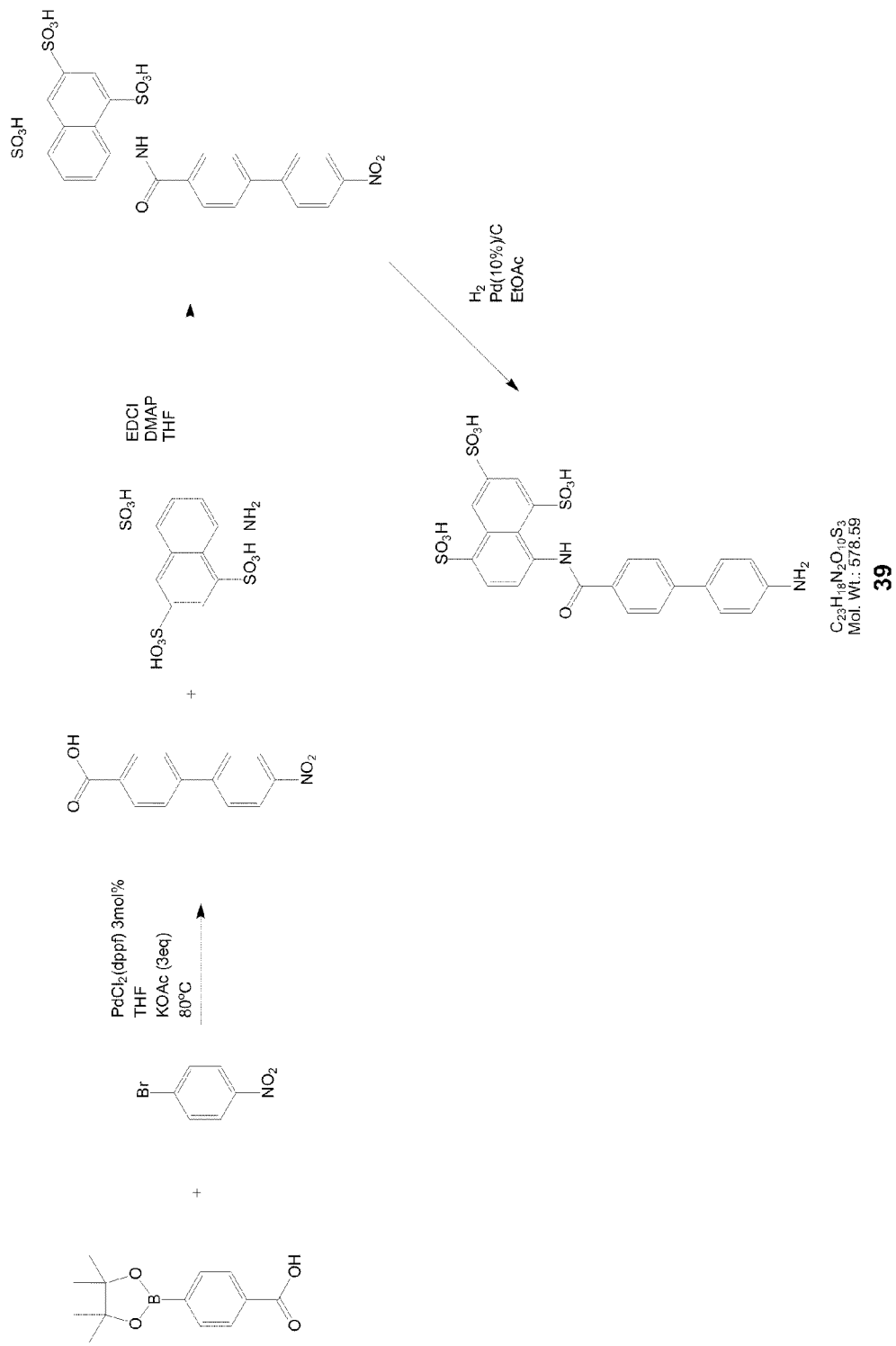
FIG. 2 is a diagram illustrating the synthesis of a representative BASA.
Figure 3:
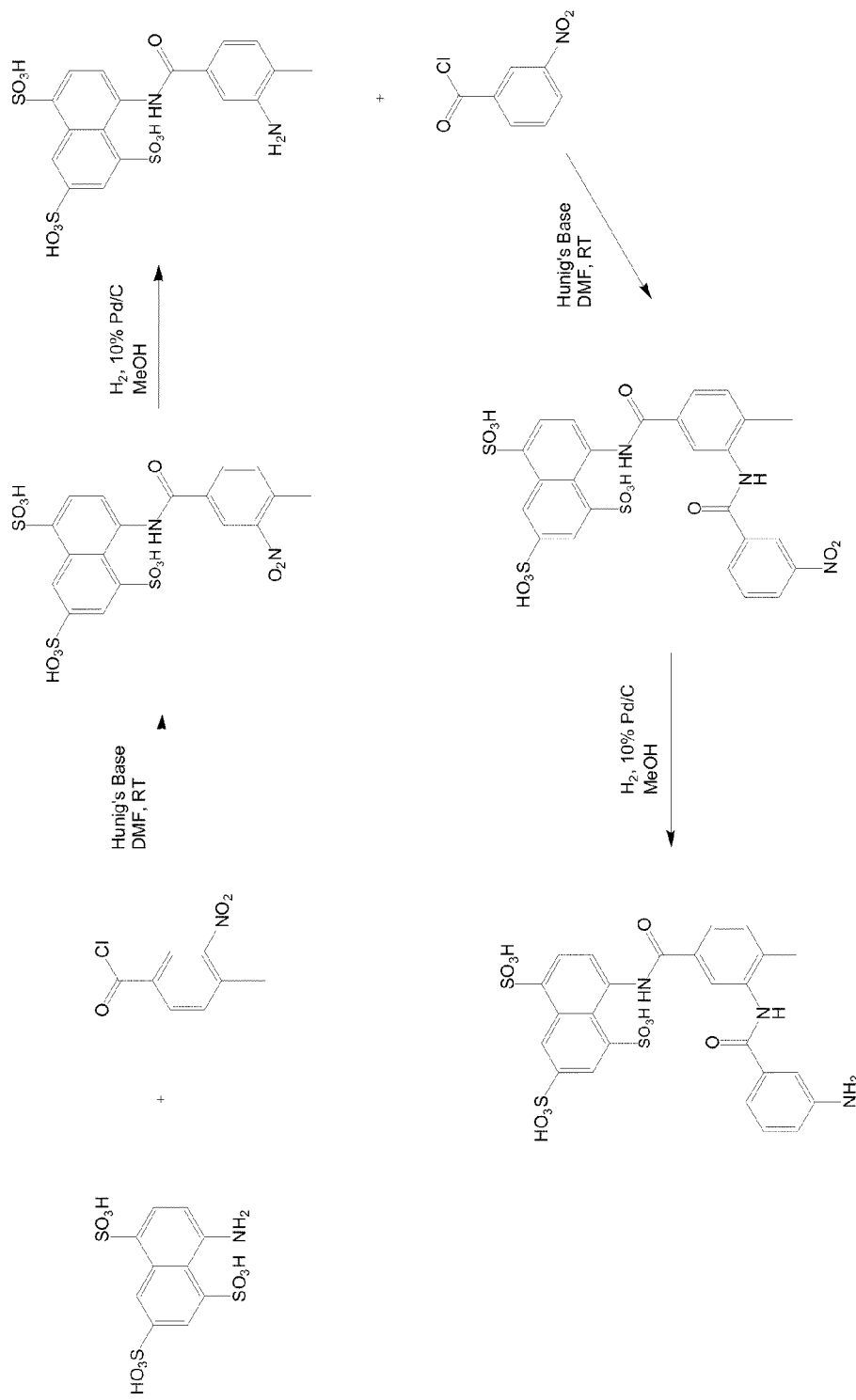
FIG. 3 is a diagram illustrating the synthesis of a representative BASA.

Certain selectin modulator components are commercially available from, for example, Sigma-Aldrich, Toronto Research Chemicals, Calbiochem and others. Others may be prepared using well known chemical synthetic techniques from available compounds. General synthetic methods for the synthesis of selectin modulators include the following: Amide formation of a primary or secondary amine or aniline can be accomplished via reaction with an acyl halide or carboxylic acid (see FIGS. 2 and 3). N-linked alkyl compounds are prepared by reductive amination of the amine/aniline with an aldehyde followed by imine reduction via sodium cyanoborohydride (see FIG. 6). Biphenyl compounds are easily prepared by reaction of suitable aryl bromide/iodides with appropriate boronic acids via Suzuki/Negishi conditions (see FIG. 2). Reduction of nitro groups can be selectively accomplished in the presence of other sensitive substrates by palladium catalyzed hydrogenation (see FIGS. 2 and 3).

Figure 1I:
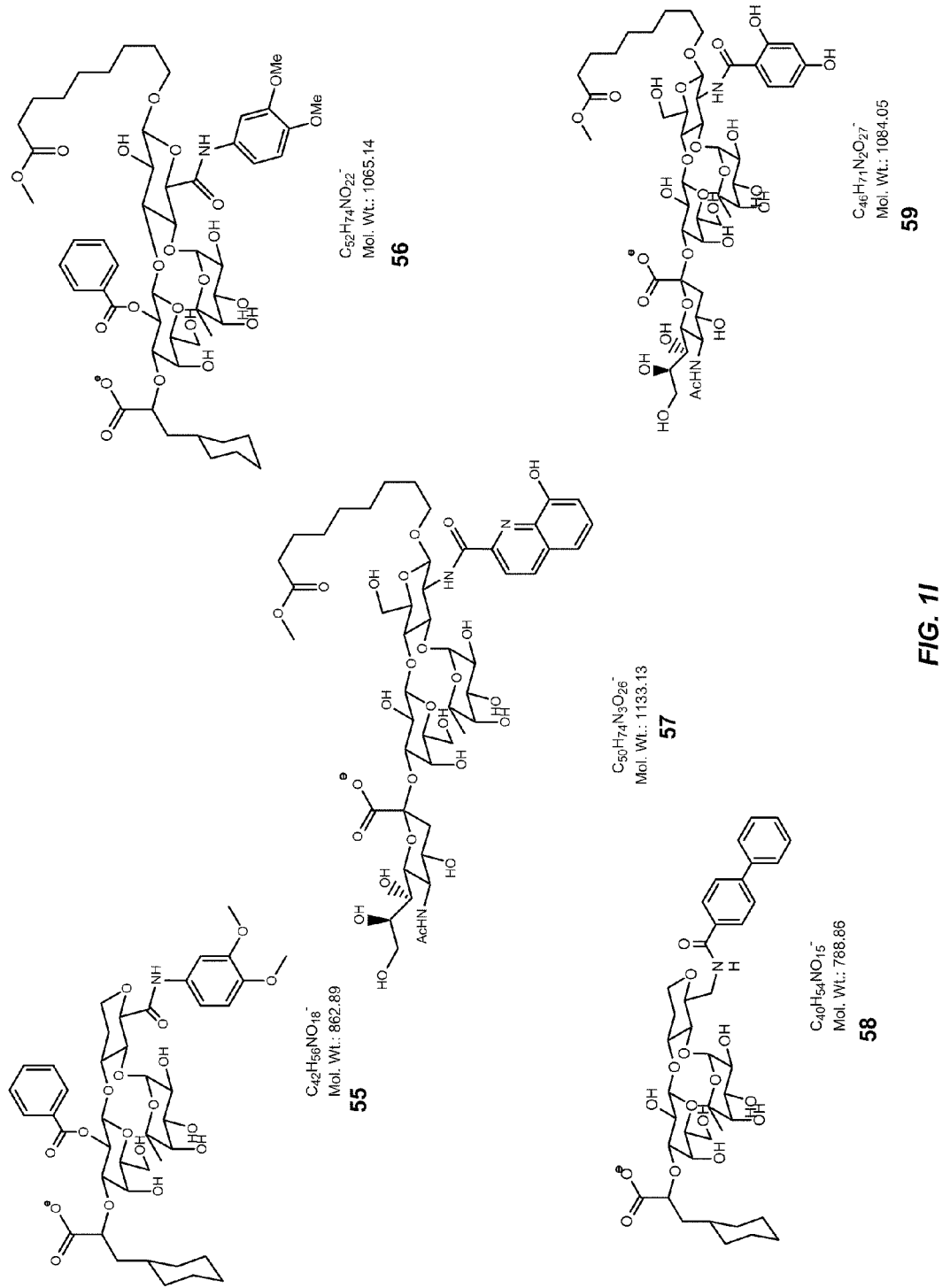

A BASA component (such as those set forth above) is linked (e.g., covalently attached with or without a spacer group) to one or more selectin binding carbohydrate moieties or glycomimetics (or glycoconjugates of either) to form a selectin modulator of the present invention. The carbohydrate moieties selected include sialyl-Lewis$^x$ (SLe$^x$), sialyl-Lewis$^a$ (SLe$^a$), and glycomimetics and glycoconjugates of these and related carbohydrates. Carbohydrate moieties comprising sialic acid-containing glycomimetics, which may be included in a selectin modulator, are found in U.S. Pat. Nos. 6,187,754B1 and 6,169,077B1 (for some structures see compounds 57 and 59 in FIG. 1I). These include glycomimetics of SLe$^x$ and SLe$^a$ with increased binding affinity for the selectins over the parent compounds. Non-sialic acid containing glycomimetics are illustrated by the compounds provided in the table on page 2897 of *Helvetica Chemica Acta* Vol. 83 (2000) and by Table 1 on page 3646 of *Angew. Chem. Int. Ed.* Vol. 40, No. 19 (2001). These glycomimetics include the replacement of sialic acid with cyclohexyllactic acid as well as additional functional group changes introduced on additional glycans (for some structures see compounds 55, 56 and 58 in FIG. 1I).

The attachment of a BASA to a carbohydrate moiety can be accomplished in a variety of ways to form a selectin modulator. The simplest carbohydrate moiety attachment method is reductive amination of the BASA to the carbohydrate moiety's reducing end (the anomeric hydroxyl/aldehyde-see FIG. 6). This is accomplished by simple reaction of the BASA to the reducing carbohydrate moiety and subsequent reduction of the imine formed. The loss of the cyclic nature of the sugar reacted with, limits the usefulness of this method. The most general approach entails the simple attachment of an activated linker to the carbohydrate moiety via an O, S or N heteroatom (or C atom for C-linked glycosides) at the anomeric position of the glycan. The methodology of such attachments has been extensively researched and anomeric selectivity is easily accomplished by proper selection of methodology and/or protecting groups. Examples of potential glycosidic synthetic methods include Lewis acid catalyzed bond formation with halogen or peracetylated sugars (Koenigs Knorr), trichloroacetamidate bond formation, thioglycoside activation and coupling, glucal activation and coupling, n-pentenyl coupling, phosphonate ester homologation (Horner-Wadsworth-Emmons reaction), and many others. Alternatively, linkers could be attached to positions on the carbohydrate moieties other than the anomeric. The most accessible site for attachment is at the six hydroxyl (6-OH) position of the sugar/sugar mimetics (a primary alcohol). The attachment of a linker at the 6-OH can be easily achieved by a variety of means. Examples include reaction of the oxyanion (alcohol anion formed by deprotonation with base) with an appropriate electrophile such as an alkyl/acyl bromide, chloride or sulfonate ester, activation of the alcohol via reaction with a sulfonate ester chloride or POCl$_3$ and displacement with a subsequent nucleophile, oxidation of the alcohol to the aldehyde or carboxylic acid for coupling, or even use of the Mitsunobu reaction to introduce differing functionalities. Once attached the carbohydrate linker is then functionalized for reaction with a suitable nucleophile on the selectin modulator (or vice versa). This is often accomplished by use of thiophosgene and amines to make thiourea-linked heterobifunctional ligands (see FIG. 4), diethyl squarate attachment (again with amines—see FIG. 5) and/or simple alkyl/acylation reactions. Additional methods that could be utilized include FMOC solid or solution phase synthetic techniques amenable for carbohydrate and peptide coupling (for novel glycopeptides and glycopeptidomimetics) and chemoenzymatic synthesis techniques possibly utilizing glycosyl/fucosyl transferases and/or oligosaccharyltransferase (OST).

Although selectin modulators as described herein may sufficiently target a desired site in vivo, it may be beneficial for certain applications to include an additional targeting moiety to facilitate targeting to one or more specific tissues. As used herein, a "targeting moiety," may be any substance (such as a compound or cell) that, when linked to a modulating agent enhances the transport of the modulator to a target tissue, thereby increasing the local concentration of the modulator. Targeting moieties include antibodies or fragments thereof, receptors, ligands and other molecules that bind to cells of, or in the vicinity of, the target tissue. Linkage is generally covalent and may be achieved by, for example, direct condensation or other reactions, or by way of bi- or multi-functional linkers.

For certain embodiments, it may be beneficial to also, or alternatively, link a drug to a selectin modulator. As used herein, the term "drug" refers to any bioactive agent intended for administration to a mammal to prevent or treat a disease or other undesirable condition. Drugs include hormones, growth factors, proteins, peptides and other compounds. Examples of potential drugs include antineoplastic agents (such as 5-fluorouracil and distamycin), integrin agonist/antagonists (such as cyclic-RGD peptide), cytokine agonist/antagonists, histamine agonist/antagonists (such as diphenhydramine and chlorpheniramine), antibiotics (such as aminoglycosides and cephalosporins) and redox active biological agents (such as glutathione and thioredoxin). In other embodiments, diagnostic or therapeutic radionuclides may be linked to a selectin modulator. In many embodiments, the agent may be linked directly or indirectly to a selectin modulator.

Evaluating Inhibition of Selectin-Mediated Intercellular Adhesion

Modulating agents as described above are capable, for example, of inhibiting selectin-mediated cell adhesion. This ability may generally be evaluated using any of a variety of in vitro assays designed to measure the effect on adhesion between selectin-expressing cells (e.g., adhesion between leukocytes and platelets or endothelial cells). For example, such cells may be plated under standard conditions that, in the absence of modulator, permit cell adhesion. In general, a modulator is an inhibitor of selectin-mediated cell adhesion if contact of the test cells with the modulator results in a discernible disruption of cell adhesion. For example, in the presence of modulators (e.g., micromolar levels), disruption of adhesion between leukocytes and platelets and/or endothelial cells may be determined visually within approximately several minutes, by observing the reduction of cells interacting with one another.

Selectin Modulator Formulations

Modulators as described herein may be present within a pharmaceutical composition. A pharmaceutical composition comprises one or more modulators in combination with one or more pharmaceutically or physiologically acceptable carriers, diluents or excipients. Such compositions may comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Within yet other embodiments, compositions of the present invention may be formulated as a lyophilizate. Compositions of the present invention may be formulated for any appropriate manner of administration, including for example, topical, oral, nasal, intravenous, intracranial, intraperitoneal, subcutaneous, or intramuscular administration.

A pharmaceutical composition may also, or alternatively, contain one or more active agents, such as drugs (e.g., those set forth above), which may be linked to a modulator or may be free within the composition.

The compositions described herein may be administered as part of a sustained release formulation (i.e., a formulation such as a capsule or sponge that effects a slow release of modulating agent following administration). Such formulations may generally be prepared using well known technology and administered by, for example, oral, rectal or subcutaneous implantation, or by implantation at the desired target site. Carriers for use within such formulations are biocompatible, and may also be biodegradable; preferably the formulation provides a relatively constant level of modulating agent release. The amount of modulating agent contained within a sustained release formulation depends upon the site of implantation, the rate and expected duration of release and the nature of the condition to be treated or prevented.

Selectin modulators are generally present within a pharmaceutical composition in a therapeutically effective amount. A therapeutically effective amount is an amount that results in a discernible patient benefit, such as increased healing of a condition associated with excess selectin-mediated function (e.g., intercellular adhesion), as described below.

Selectin Modulator Methods of Use

In general, the modulating agents and compositions described herein may be used for enhancing or inhibiting a selectin-mediated function. Such enhancement or inhibition may be achieved in vitro and/or in vivo in a warm-blooded animal, preferably in a mammal such as a human, provided that a selectin-expressing cell is ultimately contacted with a modulator, in an amount and for a time sufficient to enhance or inhibit selectin-mediated function.

Within certain aspects, the present invention provides methods for inhibiting the development of a condition associated with a selectin-mediated function, such as intercellular adhesion. In general, such methods may be used to prevent, delay or treat such a condition. In other words, therapeutic methods provided herein may be used to treat a disease, or may be used to prevent or delay the onset of such a disease in a patient who is free of disease or who is afflicted with a disease that is not associated with a selectin-mediated function.

A variety of conditions are associated with a selectin-mediated function. Such conditions include, for example, tissue transplant rejection, platelet-mediated diseases (e.g., atherosclerosis and clotting), hyperactive coronary circulation, acute leukocyte-mediated lung injury (e.g., adult respiratory distress syndrome (ARDS)), Crohn's disease, inflammatory diseases (e.g., inflammatory bowel disease), autoimmune diseases (MS, myasthenia gravis), infection, cancer (and metastasis), thrombosis, wounds (and wound-associated sepsis), burns, spinal cord damage, digestive tract mucous membrane disorders (gastritis, ulcers), osteoporosis, rheumatoid arthritis, osteoarthritis, asthma, allergy, psoriasis, septic shock, traumatic shock, stroke, nephritis, atopic dermatitis, frostbite injury, adult dyspnoea syndrome, ulcerative colitis, systemic lupus erythematosus, diabetes and reperfusion injury following ischaemic episodes. Selectin modulators may also be administered to a patient prior to heart surgery to enhance recovery. Other uses include for pain management and for undesirable angiogenesis, e.g., associated with cancer.

Selectin modulators of the present invention may be administered in a manner appropriate to the disease to be treated (or prevented). Appropriate dosages and a suitable duration and frequency of administration may be determined by such factors as the condition of the patient, the type and severity of the patient's disease and the method of administration. In general, an appropriate dosage and treatment regimen provides the modulating agent(s) in an amount sufficient to provide therapeutic and/or prophylactic benefit. Within particularly preferred embodiments of the invention, a selectin modulator may be administered at a dosage ranging from 0.001 to 100 mg/kg body weight, on a regimen of single or multiple daily doses. Appropriate dosages may generally be determined using experimental models and/or clinical trials. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

Selectin modulators may also be used to target substances to cells that express a selectin. Such substances include therapeutic agents and diagnostic agents. Therapeutic agents may be a molecule, virus, viral component, cell, cell component or any other substance that can be demonstrated to modify the properties of a target cell so as to provide a benefit for treating or preventing a disorder or regulating the physiology of a patient. A therapeutic agent may also be a prodrug that generates an agent having a biological activity in vivo. Molecules that may be therapeutic agents may be, for example, polypeptides, amino acids, nucleic acids, polynucleotides, steroids, polysaccharides or inorganic compounds. Such molecules may function in any of a variety of ways, including as enzymes, enzyme inhibitors, hormones, receptors, antisense oligonucleotides, catalytic polynucleotides, anti-viral agents, anti-tumor agents, anti-bacterial agents, immunomodulating agents and cytotoxic agents (e.g., radionuclides such as iodine, bromine, lead, palladium or copper). Diagnostic agents include imaging agents such as metals and radioactive agents (e.g., gallium, technetium, indium, strontium, iodine, barium, bromine and phosphorus-containing compounds), contrast agents, dyes (e.g., fluorescent dyes and chromophores) and enzymes that catalyze a colorimetric or fluorometric reaction. In general, therapeutic and diagnostic agents may be attached to a selectin modulator using a variety of techniques such as those described above. For targeting purposes, a selectin modulator may be administered to a patient as described herein. Since selectins are chemotactic molecules for endothelial cells involved in the formation of new capillaries during angiogenesis, a selectin modulator may be used to target a therapeutic agent for killing a tumor's vasculature. A selectin modulator may also be used for gene targeting.

Selectin modulators may also be used in vitro, e.g., within a variety of well known cell culture and cell separation methods. For example, modulators may be linked to the interior surface of a tissue culture plate or other cell culture support, for use in immobilizing selectin-expressing cells for screens, assays and growth in culture. Such linkage may be performed by any suitable technique, such as the methods described above, as well as other standard techniques. Modulators may also be used, for example, to facilitate cell identification and sorting in vitro, permitting the selection of cells expressing a selectin (or different selectin levels). Preferably, the modulator(s) for use in such methods are linked to a detectable marker. Suitable markers are well known in the art and include radionuclides, luminescent groups, fluorescent groups, enzymes, dyes, constant immunoglobulin domains and biotin. Within one preferred embodiment, a modulator linked to a fluorescent marker, such as fluorescein, is contacted with the cells, which are then analyzed by fluorescence activated cell sorting (FACS).

Although less preferred, a BASA component (i.e., BASA, portion of a BASA, analogue of a BASA, or analogue of a portion of a BASA) of a selectin modulator may be prepared alone as a pharmaceutical composition, and used in the methods above as a compound (or composition) independent of or in combination with the selectin modulators of the present invention. The above description is applied to a BASA component.

All compounds of the present invention or useful thereto, include physiologically acceptable salts thereof.

The following Examples are offered by way of illustration and not by way of limitation.

EXAMPLES

Example 1

Preparation of Representative Selectin Modulators

This Example illustrates the synthesis of representative selectin modulators or components thereof; specifically, compounds 39, 22, 60, 61, 62, and 65 (FIGS. 2 thru 7 respectively).

Synthesis of 39 (FIG. 2):
Suzuki Coupling
4-(4,4,5,5-Tetramethyl-[1,3,2]dioxaborolan-2-yl)-benzoic acid (0.004 mol, 1 eq) and KOAc (0.012 mol, 3 eq) are placed in THF (25 ml) creating a slurry.

$PdCl_2$(dppf) (0.00012 mol, 3 mol %) and p-bromo-nitrobenzene (0.005 mol, 1.2 eq) are then added to the solution with stirring and the solution is heated gently to 80° C. After 6 hrs the reaction is complete by TLC (20:1 $CH_2Cl_2$/$CH_3OH$). The reaction mixture is evaporated to dryness, dissolved in $CH_2Cl_2$ (30 ml) and washed with distilled water and saturated $NaHCO_3$. The resultant biphenyl compound is taken directly to the next step.

Carbodiimide Coupling
4'-Nitro-biphenyl-4-carboxylic acid (0.004 mol, 1 eq), dimethyl amino pyridine (1 crystal, cat.) and EDCl (0.0041 mol, 1.05 eq) are dissolved in DMF (or THF, 20 ml) and allowed to react at room temperature for 10 min. 8-Amino-naphthalene-1,3,5-trisulfonic acid is added to the reaction mixture with stirring and the reaction is allowed to proceed at room temperature under nitrogen for 48 hrs. The reaction mixture is then evaporated to dryness and purified by reverse phase chromatography (C18 column, 80/20 $CH_3CN/H_2O$-1% TFA to 50/50 $CH_3CN/H_2O$).

Hydrogenation
8-[(4'-Nitro-biphenyl-4-carbonyl)-amino]-naphthalene-1,3,5-trisulfonic acid (1 eq) and 10% Pd (10 mol %) on carbon are placed in EtOAc (or $CH_3OH$). The solution is degassed and an atmosphere of $H_2$ is generated within the reaction vessel. The reaction is allowed to proceed until the uptake of $H_2$ ceases and TLC indicates the disappearance of starting material (~12 hrs). The palladium precipitate is removed by filtration through a bed of celite and the filtrate is evaporated to dryness giving compound 39.

Synthesis of 22 (FIG. 3):
Acid Chloride Coupling
8-Amino-naphthalene-1,3,5-trisulfonic acid (0.004 mol, 1 eq) and diisopropyl ethyl amine (6 eq) are placed in DMF (20 ml) and cooled to 0° C. 3-nitro-4-methyl benzoyl chloride (0.005 mol, 1.2 eq) is dissolved in DMF and added dropwise to the cooled solution over 10 min. The reaction is allowed to proceed at 0° C. for 3 hrs. The reaction mixture is washed with 0.1M HCl (25 ml), frozen and evaporated to dryness. The resultant syrup is used without purification in the next step.

Hydrogenation
8-(4-Methyl-3-nitro-benzoylamino)-naphthalene-1,3,5-trisulfonic acid (1 eq) and 10% Pd on carbon (10 mol %) are placed in $CH_3OH$. The solution is degassed and an atmosphere of $H_2$ is generated within the reaction vessel. The reaction is allowed to proceed until the uptake of $H_2$ ceases and TLC indicates the disappearance of starting material (12 hrs). The palladium precipitate is removed by filtration through a bed of celite and the filtrate is evaporated to dryness giving the reduced compound 8-(3-Amino-4-methyl-benzoylamino)-naphthalene-1,3,5-trisulfonic acid.

Acid Chloride Coupling
8-(3-Amino-4-methyl-benzoylamino)-naphthalene-1,3,5-trisulfonic acid (0.004 mol, 1 eq) and diisopropyl ethyl amine (6 eq) are placed in DMF (15 ml) and cooled to 0° C. 3-Nitro-benzoyl chloride (0.005 mol, 1.2 eq) is dissolved in DMF (5 ml) and added dropwise to the cooled solution over 10 min. The reaction is allowed to proceed at 0° C. for 3 hrs. The reaction mixture is washed with 0.1M HCl (25 ml) and evaporated to dryness. The compound is purified by reverse phase chromatography (C18 column, 80/20 $CH_3CN/H_2O$-1% TFA to 50/50 $CH_3CN/H_2O$).

Figure 4:
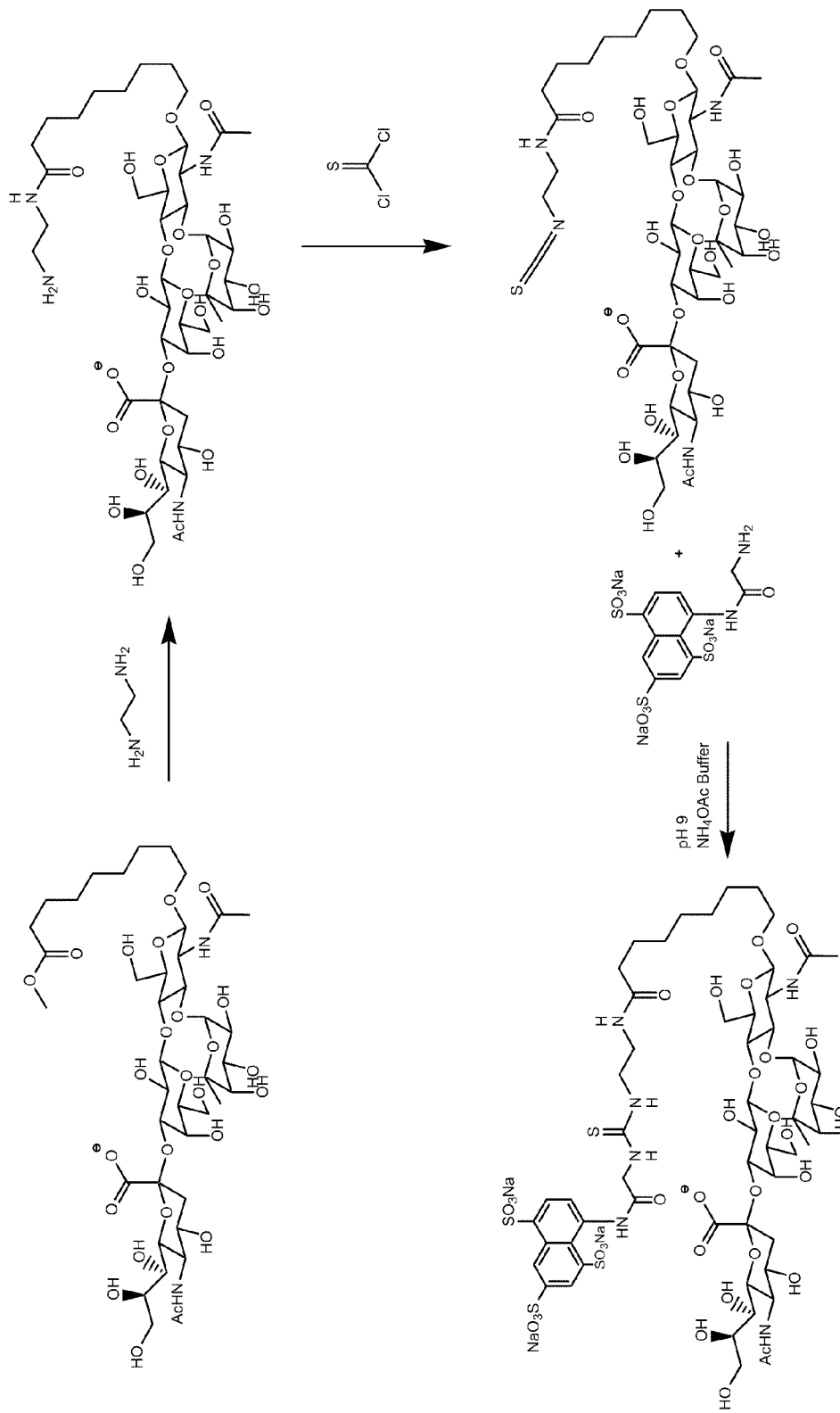
FIG. 4 is a diagram illustrating the synthesis of a BASA analogue linked to a carbohydrate moiety to form a selectin modulator of the present invention.

Synthesis of 60 (FIG. 4)

Activated Ester Synthesis

The Lemieux ester of $SLe^x$ (1 eq) is dissolved in $H_2O$ and 1,2-diaminoethane (3 eq) is added with stirring. The solution is heated to 70° C. for 50 hrs under nitrogen. The solution is evaporated to dryness and the compound purified by reverse phase chromatography (C18 column, 80/20 $CH_3CN/H_2O$-1% TFA to 50/50 $CH_3CN/H_2O$).

Thiosocyanate Formation

The Lemieux ester-amine (1 eq) is dissolved in $H_2O$ and reacted with thiophosgene (3 eq-warning highly toxic) for 3 hrs. The solution is then washed with $CH_2Cl_2$ to remove unreacted thiophosgene and the aqueous layer is collected and evaporated to dryness. The compound is used as is for the next reaction.

Formation of 60

The activated thioisocyanate (1 eq) is dissolved in an $NH_4OAc$ buffer solution of pH 9 and 8-(2-Amino-acetylamino)-naphthalene-1,3,5-trisulfonic acid (1.2 eq) is added with stirring. The reaction is allowed to stir at room temperature for 6 hrs under nitrogen. The compound is then purified by reverse phase chromatography (C18 column, 80/20 $CH_3CN/H_2O$-1% TFA to 50/50 $CH_3CN/H_2O$).

Figure 5:
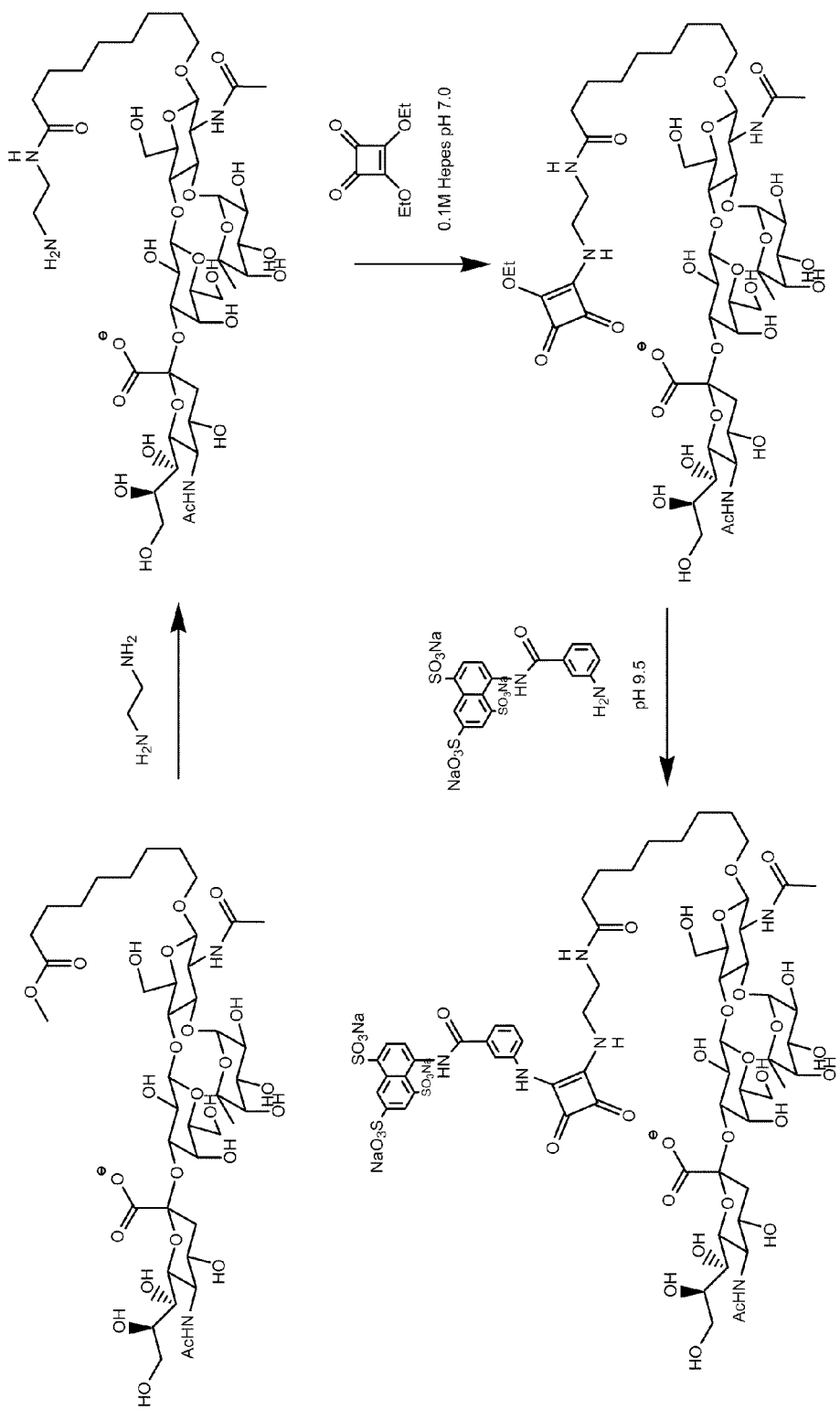
FIG. 5 is a diagram illustrating the synthesis of a BASA analogue linked to a carbohydrate moiety to form a selectin modulator of the present invention.

Synthesis of 61 (FIG. 5)

Activated Ester Synthesis

The Lemieux ester of $SLe^x$ (1 eq) is dissolved in $H_2O$ and 1,2-diaminoethane (3 eq) is added with stirring. The solution is heated to 80° C. for 50 hrs under nitrogen. The solution is evaporated to dryness and the compound purified by reverse phase chromatography (C18 column, 80/20 $CH_3CN/H_2O$-1% TFA to 50/50 $CH_3CN/H_2O$).

Squarate Ester Formation

The Lemieux ester-amine (1 eq) is dissolved in 0.1M Hepes buffer of pH 7 and reacted with squaric acid diethyl ester (3 eq) for 3 hrs. The solution is then washed with $CH_2Cl_2$ and the aqueous layer is collected and evaporated to dryness. The resultant powder is used as is in the next step.

Formation of 61

The activated squarate ester-sugar (1 eq) is dissolved in buffer of pH 9.5 and 8-(3-Amino-benzoylamino)-naphthalene-1,3,5-trisulfonic acid (1.2 eq) is added with stirring. The reaction is allowed to stir at room temperature for 6 hrs under nitrogen. The solution is evaporated to dryness and the compound is purified by reverse phase chromatography (C18 column, 80/20 $CH_3CN/H_2O$-1% TFA to 50/50 $CH_3CN/H_2O$).

Figure 6:
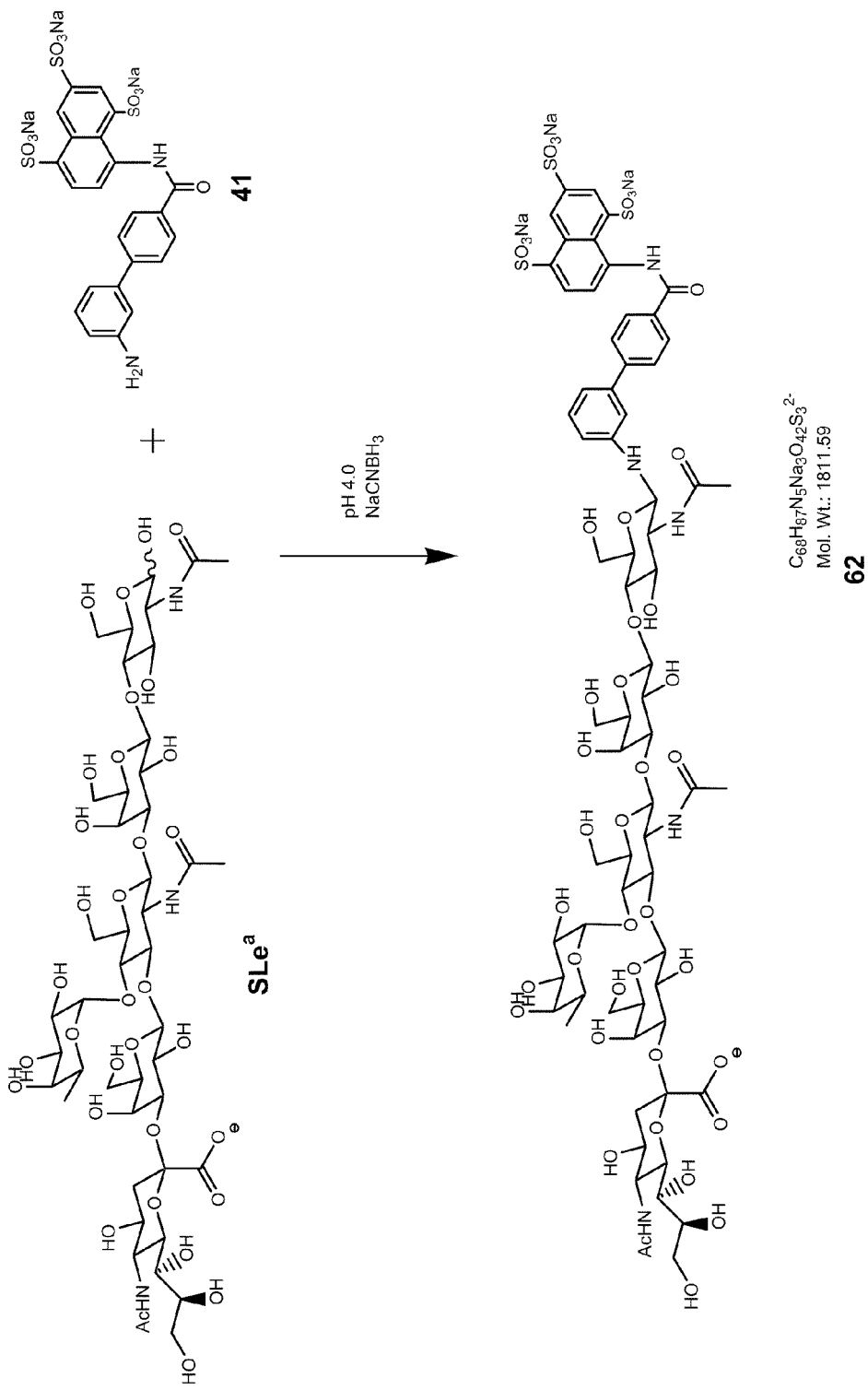
FIG. 6 is a diagram illustrating the synthesis of a BASA analogue linked to a carbohydrate moiety to form a selectin modulator of the present invention.

Synthesis of 62 (FIG. 6)

Reductive Amination $SLe^a$ (20 µmol, 1 eq) is dissolved in acetic acid buffered $H_2O$ of pH 4 (100 µl) along with BASA 41 (20 µmol, 1 eq). The reaction is allowed to proceed at room temperature under nitrogen for 12 hrs. The resultant imine formed is then reduced by reaction with $NaCNBH_3$ (30 µmol, 1.5 eq) in $CH_3CH_2OH/H_2O$ (2:1). The solution is then evaporated to dryness and purified by reverse phase chromatograpy (C18 column, 80/20 $CH_3CN/H_2O$-1% TFA to 50/50 $CH_3CN/H_2O$).

Figure 7:
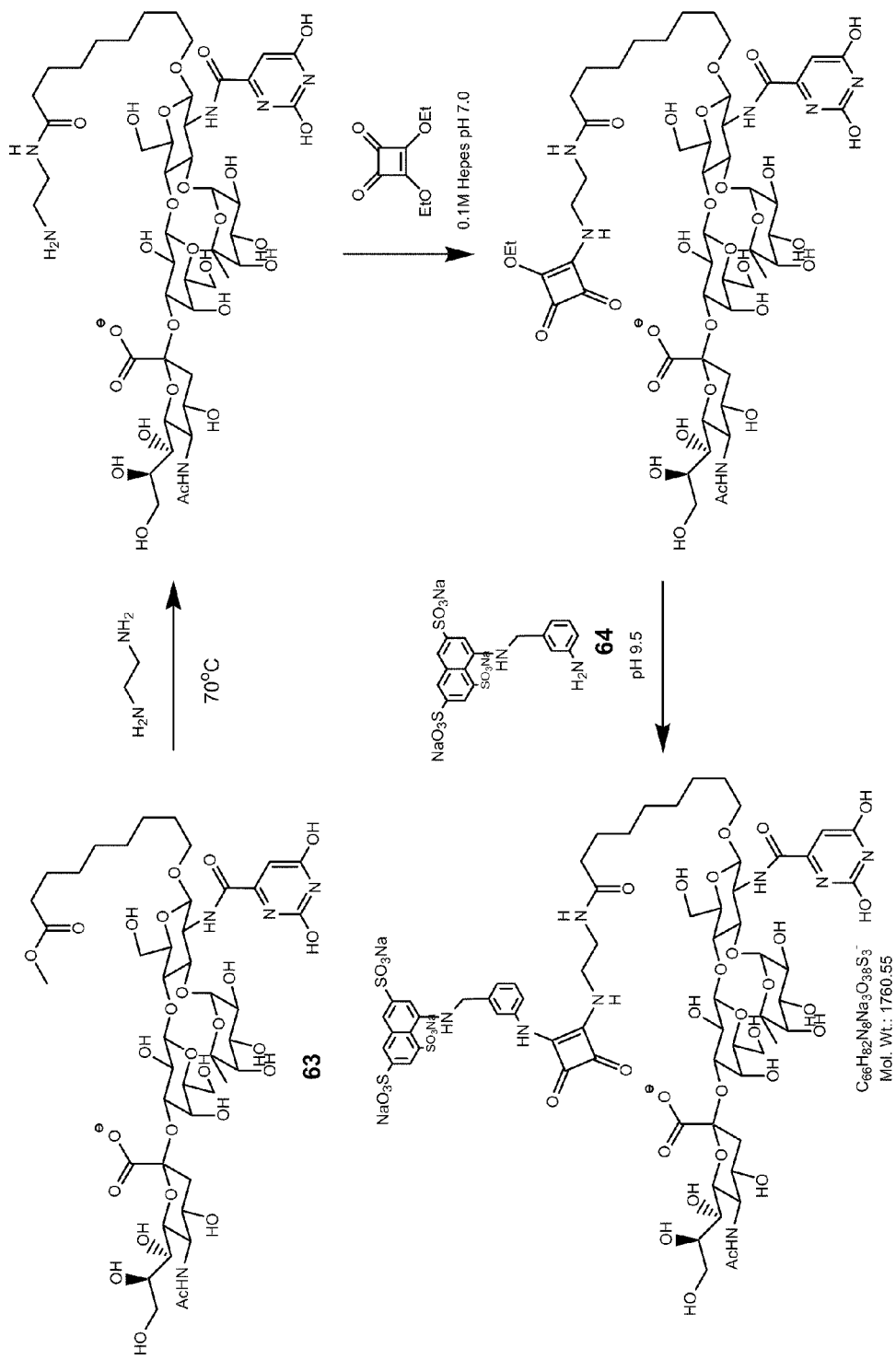
FIG. 7 is a diagram illustrating the synthesis of a BASA analogue linked to a glycomimetic to form a selectin modulator of the present invention.
Figure 8:
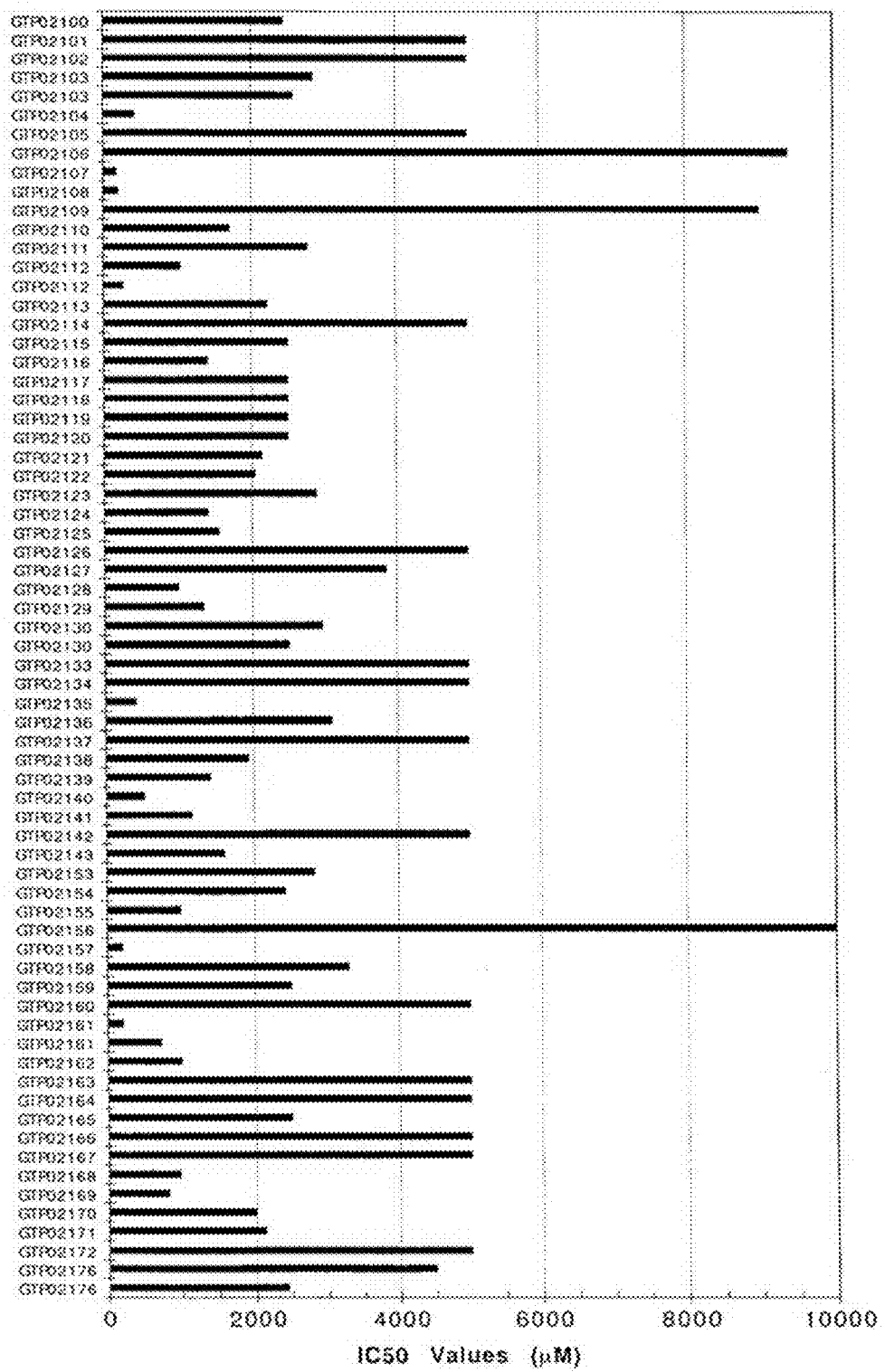
FIG. 8 is a bar graph illustrating the ability of BASA analogues to inhibit P-selectin function. Inhibition is shown as the amount of BASA analogue required to inhibit P-selectin binding in an ELISA assay by 50% ($IC_{50}$).
Figure 10:
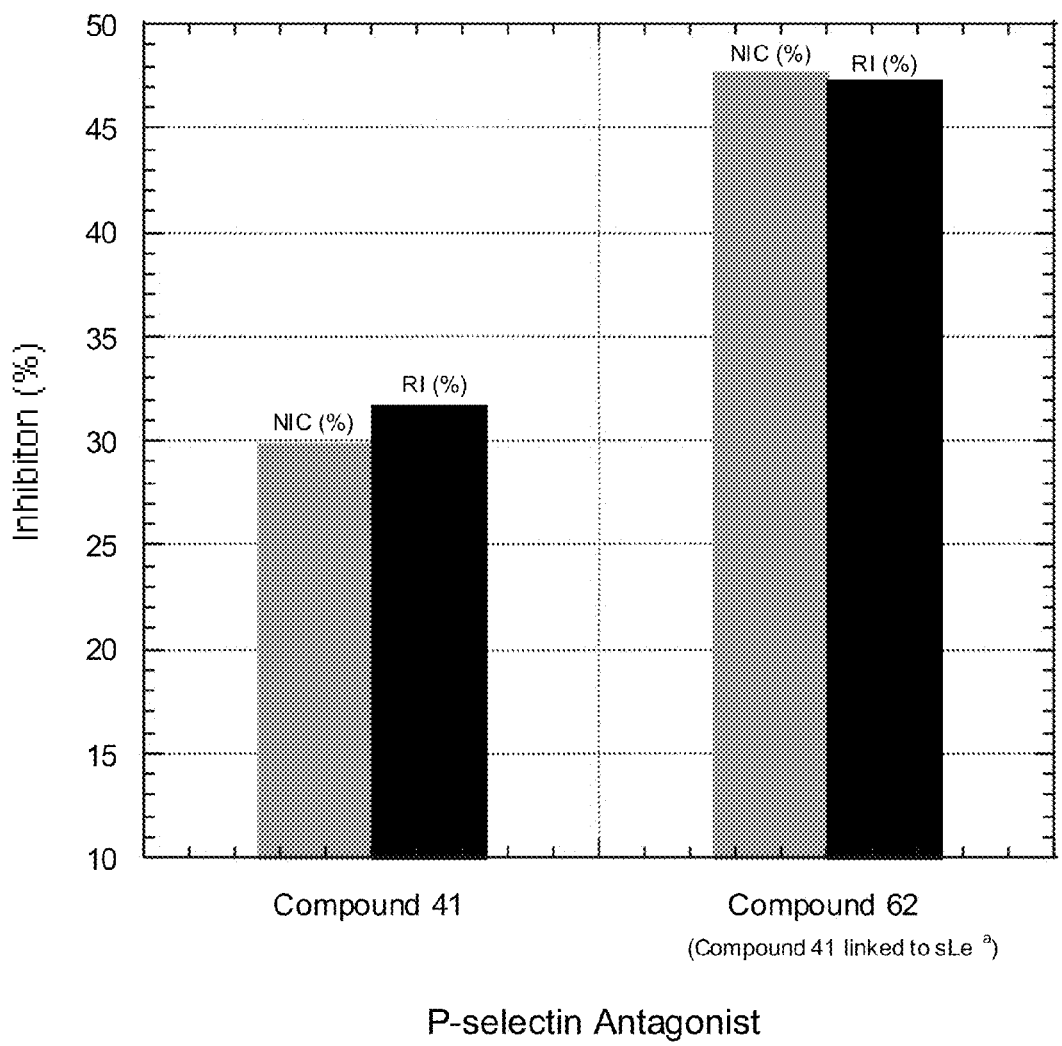
FIG. 10 is a table illustrating the inhibition of P-selectin-mediated cell adhesion under flow by a BASA analogue linked to Sialyl $Le^a$ (compound 62).
Figure 11:
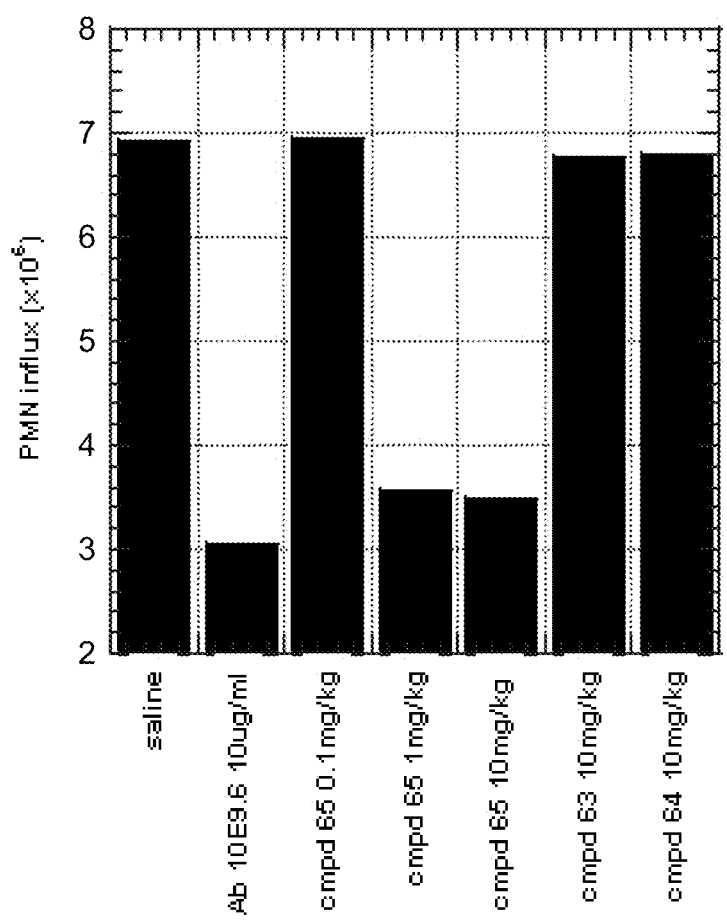
FIG. 11 is a bar graph illustrating the ability of a BASA analogue linked to a glycomimetic of Sialyl $Le^x$ (compound 65) to inhibit thioglycollate-induced peritonitis in a mouse model.

Synthesis of 65 (FIG. 7)

Activated Ester Synthesis

Compound 63 (1.8 µmol, 1 eq) is dissolved in 1,2-diaminoethane (50 µl, XS) with stirring. The solution is heated to 70° C. for 50 hrs under nitrogen. The solution is then evaporated to dryness and the compound is purified by reverse phase chromatography (C18 column, 80/20 $CH_3CN/H_2O$-1% TFA to 50/50 $CH_3CN/H_2O$).

Squarate Ester Formation

The 63-amine (5.40 µmol, 1 eq) is dissolved in 0.1M Hepes buffer of pH 7 and reacted with squaric acid diethyl ester (80 µmol, XS) for 24 hrs. The solution is then washed with $CH_2Cl_2$ and the aqueous layer is collected and evaporated to dryness. The resultant powder is purified by column chromatography (Sephadex-G25, 100% $H_2O$).

Formation of 65

The activated 63-squarate ester-sugar (5.40 µmol, 1 eq) is dissolved in $NaHCO_3$ buffer of pH 9.5 (2 ml) and BASA 64 (6.48 µmol, 1.2 eq) is added with stirring. The reaction is allowed to stir at room temperature for 3 hrs under nitrogen. The solution is evaporated to dryness and compound 65 is purified by column chromatography (Sephadex-G25, 100% $H_2O$).

Example 2

Inhibition of P-Selectin by BASE Analogues

This Example illustrates the ability of various BASA analogues to inhibit P-selectin function in ELISA and cell-based assays.

Ligand Binding Assay for P-Selectin

The neoglycoprotein SLea-HSA (IsoSep AB, Tullinge, Sweden) is incubated in wells of a 96-well microtiter plate (Falcon probind) at 100 ng/well in 50 mM Tris, 0.15M NaCl, 2 mM $CaCl_2$, pH 7.5 (TBS) overnight at 4° C. After the coating incubation, the wells are blocked with 100 µL/well of 2% bovine serum albumin (BSA) at room temperature for 2 hours.

Test compounds are serially diluted in a second 96 well plate (Plate 2; U-bottomed, low binding plate) in Dulbecco's PBS, pH 7.0 (DPBS, Biofluids, Inc.). Plate 1 is washed five times with DBPS and the contents of plate 2 are transferred to plate 1. An equal volume of P-selectin/hIg chimera (GlycoTech Corp.) is added to the wells at 4 µg/ml in 1% BSA, DPBS, pH 7.0. and the plate is incubated at room temperature for 2 hr. After incubation, the plate is washed five times and 100 µl/well of 1 µg/ml of peroxidase-labeled goat anti-human Ig (KPL labs, Gaithersburg, Md.) is added to plate 1. After incubation at room temperature for 1 hour, the plate is washed five times and TMB substrate (KPL labs, Gaithersburg, Md.) is added to each well. After five minutes the reaction is stopped by adding 100 µl/well of 1M $H_3PO_4$ and the absorbance of light at 450 nm is read by a microtiter plate reader.

Highly Sensitive Ligand Binding Assay for P-Selectin

P-selectin/hIg chimera (GlycoTech Corp., Rockville, Md.) in 50 mM Tris, 0.15M NaCl, 2 mM $CaCl_2$, pH 7.5 (TBS) is incubated in a microtiter plate (Plate 1, Falcon probind) for 2 hours at 37° C. After incubation, the plate is washed 5 times and 100 µl/well of 1% BSA in TBS is added to each well and the plate is incubated at room temperature for 1 hr.

Test compounds are serially diluted in a second round bottomed low binding plate (plate 2). An equal volume of the conjugate SLexPAAbiotin-streptavidinHRP is added to each well. The SLexPAAbiotin-streptavidinHRP is premade by mixing SLexPAA-biotin (GlycoTech Corp., Rockville, Md.) with streptavidinHRP (Sigma Chemical Co., St Louis, Mo.).

Plate 1 is washed 5 times and the contents of Plate 2 are transferred to Plate 1. After incubation for 2 hours, the plate is washed 5 times and 100 µl/well of TMB substrate (KPL labs, Gaithersburg, Md.) is added. After 10 minutes the reaction is stopped by adding 100 µl/well of 1M $H_3PO_4$ and the absorbance of light at 450 nm is read by a microtiter plate reader.

Cell-Based Assay

Human umbilical vein endothelial cells (huvecs) are isolated from umbilical cords. When the huvecs reach confluence in the T-175 flasks, they are passaged to 35mm tissue culture dishes coated with fibronectin (FN) (Gibco 33016-023). The dishes are used in 3-5 days once a confluent monolayer is obtained.

Neutrophils are isolated from fresh blood the day of each experiment and used within five hours of the isolation. The isolated PMNs are suspended in HBSS with Ca and Mg (Sigma H9269) and 12 mM Hepes (Biofluids, MD #305) at $10^7$ cells/ml for use in the flow assay.

A parallel plate flow chamber is used to study the rolling behavior which is characteristic of cells in contact with selectins in the presence of hydrodynamic flow. The parallel plate flow chamber (GlycoTech, Rockville, Md.) with a silicon rubber gasket is of a circular design to accommodate 35 mm tissue culture dishes (Corning) held in place by vacuum. The wall shear stress ($\tau_w$, dynes/cm$^2$) is given by $\tau=6 \mu Q/a^2b$, where $\mu$ is the apparent viscosity of the media (for H$_2$O@37° C.=0.0076P), a is the channel height (i.e., gasket thickness of 254 μm), b is the channel width (i.e., gasket width of 0.25 cm), and Q is the volumetric flow rate (ml/min).

Prior to the flow assay, the confluent huvec monolayers are incubated with IL-4. P-selectin antagonists and histamine are added to the PMNs prior to flow. The cell suspension of PMNs ($10^6$ cells/ml) containing the antagonists is perfused through the chamber at a shear rate corresponding to a wall shear stress of 0.9 dynes/cm$^2$. The cell suspension is allowed to flow through the chamber for three minutes before digital images are collected.

The digital image system consists of a Silicon Graphics Indigo2 workstation interfacing to Inovisionis IC300 digital image system. The PMNs interacting with the huvecs are visualized using a Zeiss inverted stage microscope (ICM 405) operated in the phase contrast mode using a 10× objective. A CCD camera is mounted on the microscope to provide the signal to the digital image system. The experiments are recorded on a video recorder. After three minutes of perfusing cells through the flow chamber, digital images are acquired at 7-10 different locations on each of three dishes for every experimental condition.

The number of interacting cells (NIC) and the number of arresting cells (NAC) are determined by a segmentation program based on pixel intensity and size. Quantification of the rolling behavior is performed by analysis of images containing the rolling cells as vertical streaks. The measure of rolling is the rolling index (RI) defined as the total area (i.e., total pixel count) of all the vertical streaks in each image. Results from the flow assay are summarized in FIG. 9. The antagonists are found to be active in the low μM range. These data confirm the ability of BASA analogues to inhibit P-selectin function.

Example 3

Thioglycollate-Induced Peritonitis in the Mouse

Peritonitis is induced in the mouse by intraperitoneal (i.p.) injection of thioglycollate (time 0, t=0). Peritonitis was allowed to develop for 4 hours. Test compounds were administered by intraperitoneal injected at t=o. Antibody to P-selectin was used as a positive control and sterile saline was used as a negative control. After 4 hours cells were removed from the peritoneal cavity by a syringe and the number of neutrophils determined. Inhibition of thioglycollate-induced peritonitis in the mouse by the heterobifunctional compound (cmpd 65) containing both glycomimetic (cmpd 63) and BASA analogue (cmpd 64) is far better than either compound alone.

From the foregoing it will be appreciated that, although specific embodiments of the invention have been described herein for purposes of illustration, various modifications may be made without deviating from the spirit and scope of the invention.

What is claimed is:

1. A compound or physiologically acceptable salt thereof, said compound being a benzyl amino sulfonic acid (BASA) linked to a glycomimetic, wherein the glycomimetic binds a selectin and is a glycomimetic of sialyl Le$^x$ or sialyl Le$^a$, and wherein the BASA has the formula:

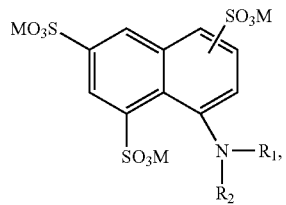

wherein each of R$_1$ and R$_2$ is independently hydrogen and R$_2$ is displaced upon linkage of the BASA via N to the glycomimetic, and M is H or is a pharmaceutically acceptable counterion.

2. The compound or physiologically acceptable salt of claim 1, wherein the sialic acid moiety in the glycomimetic of sialyl Le$^x$ or sialyl Le$^a$ is replaced with cyclohexyllactic acid.

3. A pharmaceutical composition comprising a compound or physiologically acceptable salt thereof according to claim 1 or 2 in combination with a pharmaceutically acceptable carrier or diluent.

4. The compound or physiologically acceptable salt of claim 1 or 2, wherein the physiologically acceptable salt is a sodium salt or a potassium salt.

5. A method for inhibiting a selectin-mediated function comprising contacting a cell expressing a selectin with a pharmaceutical composition according to claim 3 in an amount effective to inhibit the selectin's function.

6. A method for treating a platelet-mediated disease or a thrombosis disease in a patient in need thereof, comprising administering to said patient a pharmaceutical composition according to claim 3.

7. A method for inhibiting a selectin-mediated function comprising contacting a cell expressing a selectin with a compound or physiologically acceptable salt thereof according to claim 1 or 2 in an amount effective to inhibit the selectin's function.

8. A method of treating a platelet-mediated disease or a thrombosis disease in a patient in need thereof, comprising administering to said patient a compound or physiologically acceptable salt thereof according to claim 1 or 2.

9. A pharmaceutical composition comprising a compound or physiologically acceptable salt thereof according to claim 4 in combination with a pharmaceutically acceptable carrier or diluent.

10. A method for inhibiting a selectin-mediated function comprising contacting a cell expressing a selectin with a compound or physiologically acceptable salt thereof according to claim 4 in an amount effective to inhibit the selectin's function.

11. A method for inhibiting a selectin-mediated function comprising contacting a cell expressing a selectin with a pharmaceutical composition according to claim 9, in an amount effective to inhibit the selectin's function.

12. A method of treating a platelet-mediated disease or a thrombosis disease in a patient in need thereof, comprising administering to said patient a compound or physiologically acceptable salt thereof according to claim 4.

13. A method of treating a platelet-mediated disease or a thrombosis disease in a patient in need thereof, comprising administering to said patient a pharmaceutical composition according to claim 9.

* * * * *